(12) United States Patent
Takahashi et al.

(10) Patent No.: US 7,390,905 B2
(45) Date of Patent: Jun. 24, 2008

(54) PIPERIDINE COMPOUND AND PROCESS FOR PREPARING THE SAME

(75) Inventors: Masami Takahashi, Osaka (JP); Tsutomu Miyake, Osaka (JP); Takeshi Yamanaka, Osaka (JP); Hidetoshi Asai, Osaka (JP); Rikako Kono, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 0 days.

(21) Appl. No.: 10/581,045

(22) PCT Filed: Nov. 26, 2004

(86) PCT No.: PCT/JP2004/017543

§ 371 (c)(1),
(2), (4) Date: May 30, 2006

(87) PCT Pub. No.: WO2005/051912

PCT Pub. Date: Jun. 9, 2005

(65) Prior Publication Data

US 2007/0112029 A1 May 17, 2007

(30) Foreign Application Priority Data

Nov. 28, 2003 (JP) ............................. 2003-398368

(51) Int. Cl.
*C07D 211/30* (2006.01)
*C07D 211/32* (2006.01)
(52) U.S. Cl. ...................................... 546/226; 546/225
(58) Field of Classification Search ................ 546/226, 546/225
See application file for complete search history.

(56) References Cited

U.S. PATENT DOCUMENTS 6,951,861 B1 10/2005 Alvaro et al.

FOREIGN PATENT DOCUMENTS

| JP | 07196649 | | 8/1995 |
| WO | WO 03/066589 A1 | * | 2/2003 |
| WO | 03066589 A1 | | 8/2003 |
| WO | WO 03/066589 | * | 8/2003 |

* cited by examiner

*Primary Examiner*—D. Margaret Seaman
*Assistant Examiner*—Nizal S. Chandrakumar
(74) *Attorney, Agent, or Firm*—Browdy and Neimark

(57) ABSTRACT

The present invention relates to a piperidine compound represented by the formula [I]:

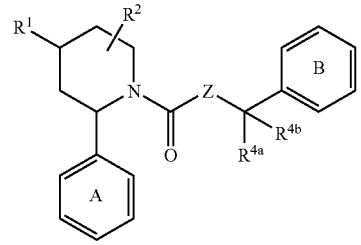

wherein Ring A represents an optionally substituted benzene ring, Ring B represents an optionally substituted benzene ring, $R^1$ represents an optionally substituted hydoxyl group, a substituted thiol group, a substituted sulfonyl group, etc., or a group represented by the formula:

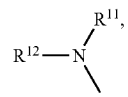

$R^{11}$ represents a substituted carbonyl group or a substituted sulfonyl group, $R^{12}$ represents hydrogen atom or an optionally substituted alkyl group, $R^2$ represents hydrogen atom, etc., Z represent oxygen atom or a group represented by —N($R^3$)—, $R^3$ represents an optionally substituted alkyl group, etc., $R^{4a}$ represents an optionally substituted alkyl group, $R^{4b}$ represents an optionally substituted alkyl group,
or a pharmaceutically acceptable salt thereof, having an excellent tachykinin receptor antagonistic action.

10 Claims, No Drawings

PIPERIDINE COMPOUND AND PROCESS FOR PREPARING THE SAME

TECHNICAL FIELD

The present invention relates to a novel piperidine compound having excellent tachykinin receptor antagonistic action.

BACKGROUND ART

Tachykinin is a general name for a group of neuropeptides, and there have been known substance P (hereinafter referred to as "SP"), neurokinin-A, and neurokinin-B in mammals. These peptides are known to exhibit a various kinds of biological activities by binding their corresponding receptors which exist in vivo (neurokinin-1, neurokinin-2, neurokinin-3). Among them, SP is one of those which have the longest history in the neuropeptides, and have been studied in detail. Its existence was confirmed in an extract of horse intestinal tube in 1931, and it was a peptide comprising 11 amino acids, whose structure was determined in 1971.

SP exists widely in central and peripheral nervous systems, and it has physiological activities such as vasodilative action, vascular permeability promoting action, smooth muscle contracting action, neuronal excitatory action, salivary action, diuretic action, immunological action, etc., as well as a function of neurotransmitter of the primary sensory neuron. Especially, it is known that SP released from the terminal of posterior horn of spinal cord upon pain impulse transfers pain information to the secondary sensory neuron, and that SP released from the peripheral terminal induces an inflammatory response via its receptors. From these facts, SP is considered to be involved in various diseases (for example, pain, inflammation, allergy, pollakiuria, urinary incontinence, respiratory disease, mental disorder, depression, anxiety, emesis, etc.), and also, SP is considered to be involved in Alzheimer-type dementia [Review: Physiological Reviews, vol. 73, pp. 229-308 (1993) (Non-Patent literature 1), Journal of Autonomic Pharmacology, vol. 13, pp. 23-93 (1993) (Non-Patent literature 2)].

[Non-Patent literature 1]
Physiological Reviews, vol. 73, pp. 229-308 (1993).
[Non-Patent literature 2]
Journal of Autonomic Pharmacology, vol. 13, pp. 23-93 (1993).

DISCLOSURE OF THE INVENTION

Problems to be Solved by the Invention

Currently, as a therapeutic agent for the above-mentioned various diseases (especially for emesis, depression, urinary disorder, etc.), there have not been discovered yet any compound having an excellent tachykinin receptor antagonistic action (specifically, SP receptor antagonistic action), and at the same time, having sufficiently satisfying safety and sustainability (metabolism, dynamics in vivo, and absorption), etc. Therefore, a compound has been sought for which has an excellent tachykinin receptor antagonistic action, and has sufficiently satisfying clinical effect as the therapeutic agent.

Means to Solve the Problems

The present invention relates to a piperidine compound represented by the formula [I]:

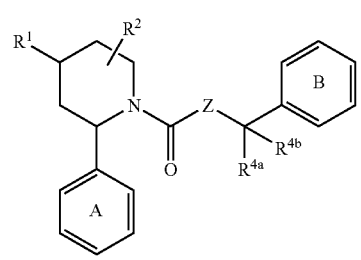

wherein Ring A represents an optionally substituted benzene ring, Ring B represents an optionally substituted benzene ring, $R^1$ represents an optionally substituted alkyl group, an optionally substituted hydroxyl group, a substituted thiol group, a substituted carbonyl group, a substituted sulfinyl group, a substituted sulfonyl group, or a group represented by the formula:

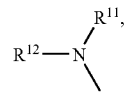

$R^{11}$ represents a substituted carbonyl group or a substituted sulfonyl group, $R^{12}$ represents hydrogen atom or an optionally substituted alkyl group, $R^2$ represents hydrogen atom, an optionally substituted hydroxyl group, an optionally substituted amino group, an optionally substituted alkyl group, a substituted carbonyl group or a halogen atom, Z represents oxygen atom or a group represented by —$N(R^3)$—, $R^3$ represents hydrogen atom or an optionally substituted alkyl group, $R^{4a}$ represents an optionally substituted alkyl group, $R^{4b}$ represents an optionally substituted alkyl group, or a pharmaceutically acceptable salt thereof.

Effects of the Invention

The present invention is to provide a compound having an excellent tachykinin receptor antagonistic action, and at the same time, satisfying clinical effects in the points of safety, in particular, sustainability (metabolism, dynamics in vivo, and absorption), etc.

BEST MODE TO CARRY OUT THE INVENTION

In the present invention, Ring A is an optionally substituted benzene ring, and a substituent of the benzene ring is exemplified by an alkyl group, a halogen atom, cyano group, optionally protected hydroxyl group or an alkoxy group. Ring A may have 1 to 3 of these substituents which may be the same or different.

In the present invention, Ring B is an optionally substituted benzene ring, and a substituent of the benzene ring may include a trihalogenoalkyl group, a halogen atom, a cyano group, phenyl group, a heterocyclic group containing 1 to 4 atoms selected from nitrogen atom, oxygen atom and sulfur atom as hetero atom(s), an alkyl group, an optionally protected hydroxyl group or an alkoxy group. Ring B may have 1 to 3 of these substituents which may be the same or different.

Preferred examples of Ring A and Ring B in the compound of the present invention may include a compound wherein Ring A is a benzene ring of the formula:

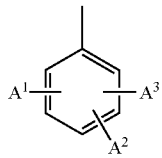

and Ring B is a benzene ring of the formula:

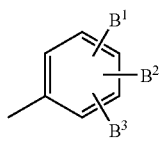

wherein $A^1$, $A^2$ and $A^3$ each may be the same or different, and represent hydrogen atom, a halogen atom, an alkyl group, an optionally protected hydroxyl or alkoxy group, $B^1$, $B^2$ and $B^3$ each may be the same or different, and are hydrogen atom, a trihalogenoalkyl group, a halogen atom, a cyano group, a phenyl group, a heterocyclic group containing 1 to 4 atoms selected from nitrogen atom, oxygen atom and sulfur atom as hetero atom(s), an alkyl group, an optionally protected hydroxyl or an alkoxy group. The trihalogenoalkyl group may include a trifluoromethyl group or a trichloromethyl group, etc. The heterocyclic group having 1 to 4 atoms selected from nitrogen atom, oxygen atom and sulfur atom as a hetero atom(s) may include tetrazolyl group.

In the present invention, a protecting group of the optionally protected hydroxyl group may include a conventional protection group such as an optionally substituted arylalkyl group, an optionally substituted silyl group and an acyl group. In the above, preferred are an arylalkyl group such as benzyl group and phenethyl group, a substituted silyl group such as tert-butyldimethylsilyl group and tert-butyldiphenylsilyl group, and an acyl group such as formyl group, acetyl group, propionyl group, malonyl group, acryloyl group and benzoyl group.

In the present invention, $R^1$ is an optionally substituted alkyl group, an optionally substituted hydroxyl group, a substituted thiol group, a substituted carbonyl group, a substituted sulfinyl group, a substituted sulfonyl group, or a group represented by the formula:

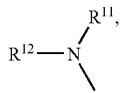

$R^{11}$ is a substituted carbonyl group or a substituted sulfonyl group, and $R^{12}$ is hydrogen atom or an optionally substituted alkyl group.

Of these, it is preferred that $R^1$ is an optionally substituted hydroxyl group, a substituted thiol group, a substituted sulfonyl group, or a group represented by the formula:

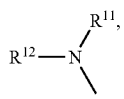

$R^{11}$ is a substituted carbonyl group, and $R^{12}$ is hydrogen atom or an alkyl group.

In the present invention, substituent(s) of the optionally substituted alkyl group of $R^1$ may include an alkoxycarbonyl group, morpholinoaminocarbonyl group, a dialkylaminocarbonyl group, hydroxyl group, a hydroxyalkylaminocarbonyloxy group or an alkylpiperazinocarbonyl group.

In the present invention, substituent(s) of the optionally substituted hydroxyl group of $R^1$ may include (1) a substituted carbonyl group,
(2) a substituted sulfinyl group,
(3) a substituted sulfonyl group or
(4) an optionally substituted alkyl group.

Substituent(s) of the substituted carbonyl group of the above-mentioned (1) may include an optionally substituted alkyl group, an optionally substituted alkoxy group, an optionally substituted amino group, a monocyclic heterocyclic group having 1 or 2 atoms selected from nitrogen atom and oxygen atom as a hetero atom(s) (the monocyclic heterocyclic group may have a substituent(s).). Substituent(s) of the optionally substituted alkyl group may include hydroxyl group. Substituent(s) of the optionally substituted alkoxy group may include an alkoxy group, hydroxyl group or a halogen atom. Substituent(s) of the optionally substituted amino group may include an alkyl group which may be substituted by a group(s) selected from carboxyl group, morpholinocarbonyl group, a dialkylaminocarbonyl group, an alkylaminocarbonyl group, an alkanoyl-amino group, an alkylthio group, an alkoxy group, an alkylsulfonyl group, an alkanoyloxy group and hydroxyl group; piperidinyl group substituted by a hydroxyalkanoyl group or an alkoxyalkanoyl group; or a dialkylaminosulfonyl group. The monocyclic heterocyclic group may include morpholino group, imidazolyl group, thiomorpholino group, piperidino group, furyl group, tetrahydrothiazolinyl group or pyrrolidinyl group. Substituent(s) of the monocyclic heterocyclic group may include hydroxyl group, a hydroxyalkyl group, an alkoxycarbonyl group, carboxyl group, a hydroxyalkylaminocarbonyl group, an alkoxyalkylaminocarbonyl group, an alkylthioalkylaminocarbonyl group, an alkylsulfinylalkylaminocarbonyl group, an alkylsulfonylalkylaminocarbonylalkyl group, oxo group or hydroxyl group.

Substituent(s) of the substituted sulfinyl group of the above-mentioned (2) may include an alkyl group or thienyl group.

Substituent(s) of the substituted sulfonyl group of the above-mentioned (3) may include an alkyl group or thienyl group.

Substituent(s) of the optionally substituted alkyl group of the above-mentioned (4) may include an optionally substituted hydroxyl group, a dialkylamino group or a monocyclic heterocyclic group having 1 to 4 atoms selected from nitrogen atom, oxygen atom and sulfur atom as a hetero atom(s) (the monocyclic heterocyclic group may have a substituent(s)). Substituent(s) of the optionally substituted hydroxyl group may include an alkyl group, an alkylsulfonyl group or tetrahydropyranyl group. The monocyclic heterocyclic group may include triazolyl group or tetrazolyl group. Substituent(s) of the monocyclic heterocyclic group may include an alkyl group.

In the present invention, substituent(s) of the optionally substituted thiol group of $R^1$ may include a substituted pyrimidinyl group, a substituted carbonyl group or an optionally substituted alkyl group. Substituent(s) of the substituted pyrimidinyl group may include hydroxyl group. Substituent(s) of the substituted carbonyl group may include an alkyl group. Substituent(s) of the optionally substituted alkyl group may include an alkylaminocarbonyl group, a dialkylaminocarbonyl group, alkoxycarbonylamino group, a hydroxyalkanoylamino group, morpholinocarbonylamino group, a hydroxyalkylaminocarbonylamino group, an alkanoyloxy group or hydroxyl group.

In the present invention, substituent(s) of the substituted carbonyl group of $R^1$ may include hydroxyl group, an alkoxy group, an optionally substituted amino group or a monocyclic heterocyclic group having 1 to 4 atoms selected from nitrogen atom, oxygen atom and sulfur atom as a hetero atom(s) (the monocyclic heterocyclic group may have a substituent(s)). Substituent(s) of the optionally substituted amino group may include a pyridyl group substituted by hydroxyl group, pyrimidinyl group, alkylpyrido group, or an alkyl group optionally substituted by hydroxyl group or cyano group. Substituent(s) of the amino group may be mono or di-substituted on the amino group. The monocyclic heterocyclic group may include piperidino group, piperadino group, morpholino group, thiomorpholino group or pyrrolidino group. Substituent(s) of the monocyclic heterocyclic group may include an alkyl group, hydroxyl group, oxo group, pyrimidinyl group, an alkylsulfonyl group, alkanoyl group or hydroxyalkyl group.

In the present invention, substituent(s) of the substituted sulfinyl group of $R^1$ may include hydroxyl group or an optionally substituted alkyl group. Substituent(s) of the optionally substituted alkyl group may include hydroxyl group.

In the present invention, substituent(s) of the substituted sulfonyl group of $R^1$ may include an optionally substituted alkyl group. Substituent(s) of the optionally substituted alkyl group may include hydroxyl group or an alkanoyloxy group.

In the present invention, when $R^1$ is a group represented by the formula:

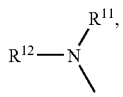

(1) substituent(s) of the substituted carbonyl group of $R^{11}$ may include an optionally substituted alkyl group, an optionally substituted alkoxy group, an optionally substituted aryl group, an optionally substituted amino group, or a heterocyclic group having 1 to 4 atoms selected from nitrogen atom, oxygen atom and sulfur atom as a hetero atom(s), the heterocyclic group may have a substituent(s), and the nitrogen atom or the sulfur atom contained in the heterocyclic group may be oxidized. Substituent(s) of the optionally substituted alkyl group may include an alkanoyl group, benzyloxy group, an alkylaminocarbonyl group, a dialkylaminocarbonyl group an alkyl portion of which may be substituted by hydroxyl group, aminocarbonyl group, an alkoxycarbonylamino group, an alkanoylamino group, an amino group substituted by an alkoxycarbonyl group and an alkyl group, an amino group substituted by an alkanoyl group and an alkyl group, an alkoxy group, a halogen atom, tetrazolyl group, furyl group, hydroxyl group, an alkylthio group, 2-aminothiazolyl group, 2-thiol-4-alkylthiazolyl group, cycloalkyl group, an alkylsulfinyl group, an alkylsulfonyl group, thienyl group or 5-methyl-2,4(1H, 3H)pyrimidinedione group. Substituent(s) of the optionally substituted alkoxy group may include an alkoxy group, a halogen atom or hydroxyl group. Substituent(s) of the optionally substituted aryl group may include nitro group or amino group, the aryl group may include phenyl group, naphthyl group, phenanthryl group or anthracenyl group, etc. Substituent(s) of the optionally substituted amino group may include an alkyl group which may be substituted by a group(s) selected from a halogen atom, an alkoxy group and hydroxyl group, and may be mono-substituted or di-substituted. The heterocyclic group may include a saturated or unsaturated monocyclic or bicyclic heteroaromatic ring group, and may include, for example, thienyl group, furyl group, tetrahydrofuryl group, pyranyl group, pyrrolyl group, imidazolyl group, pyrazolyl group, isothiazolyl group, isoxazolyl group, pyridyl group, pyrazinyl group, pyrimidinyl group, pyridazinyl group, pyrrolidinyl group, pyrrolinyl group, imidazolidinyl group, imidazolinyl group, pyrazolidinyl group, pyrazolinyl group, piperidyl group, piperazinyl group, morpholinyl group, thiomorpholinyl group, benzothienyl group, benzofuryl group, isobenzofuranyl group, chromenyl group, indolyl group, isoindolyl group, indazolyl group, purinyl group, quinolidinyl group, naphthyridinyl group, quinoxalinyl group, cinnolinyl group, quinolyl group, isoquinolyl group, benzothiazolyl group, benzisothiazolyl group, quinazolinyl group, phthalazinyl group, benzoxazolyl group, benzimidazolyl group, pteridinyl group, pyridopyrimidinyl group, isochromanyl group, chromanyl group, indolinyl group, isoindolinyl group, tetrahydroquinolyl group, tetrahydroisoquinolyl group, tetrahydroquinoxalinyl group, dihydrophthalazinyl group, etc. of these heterocyclic groups, thienyl group, furyl group, tetrahydrofuryl group, pyridyl group, pyrrolidinyl group, piperidinyl group, piperazinyl group, morpholino group, thiomorpholino group, etc. are preferably used. Substituent(s) of the heterocyclic group may include an alkoxycarbonyl group, an alkyl group, benzyloxy group, an alkoxycarbonyl group, alkanoyl group, hydroxyl group, oxo group or formyl group.

(2) Substituent of the substituted sulfonyl group may include an optionally substituted alkyl group, dialkylamino group, or an alkenyl group. The substituent of the optionally substituted alkyl group may include a halogen atom or hydroxyl group.

In the present invention, $R^2$ is hydrogen atom, an optionally substituted hydroxyl group, an optionally substituted amino group, an optionally substituted alkyl group, a substituted carbonyl group or a halogen atom.

In the present invention, substituent(s) of the optionally substituted hydroxyl group of $R^2$ may include an alkyl group.

In the present invention, substituent(s) of the optionally substituted amino group of $R^2$ may include an alkyl group.

In the present invention, substituent(s) of the optionally substituted alkyl group of $R^2$ may include an alkoxy group.

In the present invention, substituent(s) of the substituted carbonyl group of $R^2$ may include hydroxyl group, an alkoxy group or an alkylamino group.

In the present invention, Z is oxygen atom or a group represented by —N($R^3$)—.

In the present invention, $R^3$ may include hydrogen atom or an optionally substituted alkyl group. Substituent(s) of the optionally substituted alkyl group of $R^3$ may include hydroxyl group, alkanoyl group, a halogen atom, an alkoxy group or alkylamino group.

In the present invention, $R^{4a}$ may include an optionally substituted alkyl group.

In the present invention, $R^{4b}$ may include an optionally substituted alkyl group.

As the compound of the present invention, $R^1$ is preferably an optionally substituted alkyl group. Substituent(s) of the alkyl group is preferably a dialkylaminocarbonyl group, morpholinocarbonyl group, hydroxyl group, an alkoxycarbonyl group or a hydroxyalkylaminocarbonyloxy group.

As the compound of the present invention, a compound in which $R^1$ is an optionally substituted hydroxyl group is preferred. Of these, a compound in which $R^1$ is an optionally substituted alkoxy group is preferred. Of these, a compound in which it is a substituted carbonyloxy group is preferred. Substituent(s) of the alkoxy group preferably include hydroxyl group, an alkylsulfonyloxy group, tetrahydropyranyloxy group, triazolyl group, tetrazolyl group which may be substituted by an alkyl group, or an alkoxy group, and hydroxyl group or tetrahydropyranyloxy group is more preferred. Substituent(s) of the carbonyloxy group may preferably include morpholino group; imidazolyl group; an alkylamino group an alkyl group portion of which may be substituted by hydroxyl group, morpholinocarbonyl group, a dialkylaminocarbonyl group, an alkylaminocarbonyl group, an alkylthio group, an alkoxy group, an alkylsulfonyl group, an alkanoyloxy group or carboxyl group; a piperidino group substituted by hydroxyl group, an alkoxycarbonyl group, carboxyl group, a hydroxyalkylaminocarbonyl group, an alkoxyalkylaminocarbonyl group, an alkylthioalkylaminocarbonyl group, an alkylsulfinylalkylaminocarbonyl group, an alkylsulfonylalkylaminocarbonyl group or a hydroxyalkyl group; a piperidinylamino group substituted by a hydroxyalkanoyl group or an alkoxyalkanoyl group; a thiomorpholino group the sulfur atom of which may be oxidized; oxopyrrolidinyl group; oxotetrahydrothiazolinyl group; or a dialkylaminosulfonylamino group, and an alkylamino group the alkyl portion of which is substituted by hydroxyl group is more preferred.

As the compound of the present invention, a compound in which $R^1$ is a substituted thiol group is preferred. Substituent(s) of the thiol group may preferably include an alkanoyl group; or an alkyl group optionally substituted by hydroxyl group, an alkylaminocarbonyl group, a dialkylaminocarbonyl group, an alkoxycarbonylamino group, a hydroxyalkanoylamino group, morpholinocarbonylamino group, a hydroxyalkylaminocarbonylamino group or an alkanoyloxy group, and an alkyl group substituted by hydroxyl group is more preferred.

As the compound of the present invention, a compound in which $R^1$ is a substituted carbonyl group is preferred. Substituent(s) of the carbonyl group may preferably include hydroxyl group; an alkoxy group; pyrimidylamino group; an amino group substituted by an alkylpyrido group and an alkyl group; an alkylamino group the alkyl group portion of which may be substituted by hydroxyl group or cyano group; a di(hydroxyalkyl)amino group; a pyridylamino group the pyridyl group portion of which may be substituted by hydroxyl group; a piperidino group substituted by hydroxyl group or oxo group; a piperadino group substituted by oxo group, an alkyl group, an alkylsulfonyl group or an alkanoyl group; morpholino group; thiomorpholino group; or a pyrrolidino group substituted by hydroxyalkyl group or hydroxyl group, and pyrimidinylamino group or hydroxypiperadino group is more preferred.

As the compound of the present invention, a compound in which $R^1$ is a substituted sulfinyl group is preferred. Substituent(s) of the sulfinyl group may preferably include an alkyl group optionally substituted by hydroxyl group, or hydroxyl group is preferred, and an alkyl group optionally substituted by hydroxyl group is more preferred.

As the compound of the present invention, a compound in which $R^1$ is a substituted sulfonyl group is preferred. Substituent(s) of the sulfonyl group may preferably include hydroxyl group or an alkyl group optionally substituted by an alkanoyloxy group is preferred, and an alkyl group substituted by hydroxyl group is more preferred.

As the compound of the present invention, a compound in which $R^1$ is a group represented by the formula:

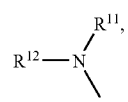

$R^{11}$ is a substituted carbonyl group or a substituted sulfonyl group, $R^{12}$ is hydrogen atom or an alkyl group is preferred. Of these, a compound in which $R^{11}$ is a substituted carbonyl group, and $R^{12}$ is hydrogen atom or an alkyl group is preferred, and a compound in which $R^{11}$ is an optionally substituted alkanoyl group, an optionally substituted aminocarbonyl group, morpholinocarbonyl group, or a piperidinylcarbonyl group optionally substituted by an alkanoyl group is each preferred. Of these, in addition, $R^{11}$ is a substituted sulfonyl group, and $R^{12}$ is hydrogen atom or alkyl group is also preferred. Substituent(s) of the alkanoyl group may preferably include an alkanoyl group, an alkylaminocarbonyl group, a dialkylaminocarbonyl group, aminocarbonyl group, an alkoxycarbonylamino group, an alkanoylamino group, an amino group substituted by an alkoxycarbonyl group and an alkyl group, an amino group substituted by an alkanoyl group and an alkyl group, an alkoxy group optionally substituted by phenyl group, furyl group, tetrazolyl group, hydroxyl group, an alkylthio group, an alkylsulfinyl group, an alkylsulfonyl group, 2-aminothiazolyl group, 2-oxopyrrolidino group, a 2-thiol-4-alkylthiazolidinyl group or cycloalkyl group, and hydroxyl group is more preferred. Substituent(s) of the aminocarbonyl group may preferably include an alkyl group optionally substituted by a halogen atom, hydroxyl group or an alkoxy group, and an alkyl group is more preferred. Substituent(s) of the sulfonyl group may preferably include an alkyl group optionally substituted by hydroxyl group or a halogen atom, an alkenyl group or a dialkylamino group, and an alkyl group is more preferred.

As Compound [I] of the present invention, there may be mentioned a compound in which Ring A is a benzene ring represented by the formula:

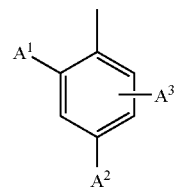

Ring B is a benzene ring represented by the formula:

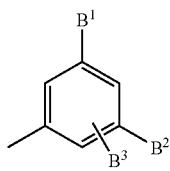

A¹ is hydrogen atom, a halogen atom, alkyl group or an alkoxy group, A² is hydrogen atom or a halogen atom, A³ is hydrogen atom, B¹ is hydrogen atom, an alkyl group, a halogen atom, cyano group, an alkoxy group or a trihalogenoalkyl group, B² is hydrogen atom, an alkyl group, a halogen atom, cyano group, an alkoxy group or a trihalogenoalkyl group, B³ is hydrogen atom, R¹ is hydroxyl group; an alkyl group substituted by a dialkylaminocarbonyl group, morpholinocarbonyl group, hydroxyl group, an alkoxycarbonyl group, morpholinoaminocarbonyl group, a hydroxyalkylaminocarbonyloxy group, or an alkylpiperazinocarbonyl group; dihydroxypyrimidinylthio group; an alkanoylthio group; an alkylthio group optionally substituted by hydroxyl group, an alkylaminocarbonyl group, a dialkylaminocarbonyl group, an alkoxycarbonylamino group, a hydroxyalkanoylamino group, morpholinocarbonylamino group, a hydroxyalkylaminocarbonylamino group or an alkanoyloxy group; a dialkylthionium group; hydroxyl group, an alkylsulfonyloxy group, tetrahydropyranyloxy group, triazolyl group, a tetrazolyl group optionally substituted by an alkyl group or an alkoxy group optionally substituted by an alkoxy group; morpholinocarbonyloxy group; imidazolylcarbonyloxy group; an alkylaminocarbonyloxy group the alkyl group portion of which may be substituted by hydroxyl group, morpholinocarbonyl group, a dialkylaminocarbonyl group, an alkylaminocarbonyl group, an alkanoylamino group, an alkylthio group, an alkoxy group, an alkylsulfonyl group, an alkanoyloxy group or carboxyl group; a piperidinocarbonyloxy group substituted by hydroxyl group, an alkoxycarbonyl group, carboxyl group, a hydroxyalkylaminocarbonyl group, an alkoxyalkylaminocarbonyl group, an alkylthioalkylaminocarbonyl group, an alkylsulfinylalkylaminocarbonyl group, an alkylsulfonylalkylaminocarbonyl group or a hydroxyalkyl group; a dialkylaminocarbonyloxy group substituted by hydroxyl group; a piperidinylaminocarbonyloxy group substituted by a hydroxyalkanoyl group or an alkoxyalkanoyl group; a thiomorpholinocarbonyloxy group the sulfur atom of which may be substituted by oxo group; oxopyrrolidinylcarbonyloxy group; oxotetrahydrothiazolinylcarbonyloxy group; a dialkylaminosulfonylaminocarbonyloxy group; carboxyl group; an alkoxycarbonyl group; pyrimidinylaminocarbonyl group; an alkylaminocarbonyl group the alkyl group portion of which may be substituted by hydroxyl group or cyano group; a di(hydroxyalkyl)aminocarbonyl group; a pyridylaminocarbonyl group the pyridyl group portion of which is substituted by hydroxyl group; an aminocarbonyl group substituted by an alkylpyrido group and an alkyl group; a piperidinocarbonyl group substituted by hydroxyl group or oxo group; a piperadinocarbonyl group substituted by oxo group, an alkyl group, pyrimidinyl group, an alkylsulfonyl group or an alkanoyl group; morpholinocarbonyl group; a thiomorpholinocarbonyl group the sulfur atom of which may be oxidized; a pyrrolidinocarbonyl group substituted by a hydroxyalkyl group or hydroxyl group; an alkylsulfinyl group optionally substituted by hydroxyl group; hydroxysulfinyl group; an alkylsulfonyl group optionally substituted by hydroxyl group or an alkanoyloxy group; or a group represented by the formula:

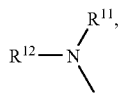

R¹¹ is an alkanoyl group optionally substituted by a group selected from an alkanoyl group, an alkylaminocarbonyl group, a dialkylaminocarbonyl group, aminocarbonyl group, an alkoxycarbonylamino group, an alkanoylamino group, an amino group substituted by an alkoxycarbonyl group and an alkyl group, an amino group substituted by an alkanoyl group and an alkyl group, an alkoxy group optionally substituted by a halogen atom or phenyl group, tetrazolyl group, hydroxyl group, an alkylthio group, alkylsulfinyl group, an alkylsulfonyl group, 2-aminothiazolyl group, 2-oxopyrrolidino group, 2,2-dialkyl-1,3-dioxylanyl group, 2-thiol-4-alkylthiazolinyl group, cycloalkyl group and 5-alkyl-2,4(1H,3H)pyrimidinedione group; a phenylcarbonyl group optionally substituted by amino group or nitro group; a pyridylcarbonyl group optionally substituted by an alkyl group or hydroxyl group; a furylcarbonyl group optionally substituted by formyl group or a hydroxyalkyl group; thienylcarbonyl group; a pyrazinylcarbonyl group substituted by an alkanoyl group; morpholinocarbonyl group; a pyrrolidinylcarbonyl group optionally substituted by benzyloxy group, an alkoxycarbonyl group, an alkanoyl group, hydroxyl group or oxo group; tetrahydrofurylcarbonyl group; a piperidinylcarbonyl group substituted by an alkoxycarbonyl group or an alkanoyl group; a thiomorpholinocarbonyl group the sulfur atom of which may be substituted by oxo group; 3-alkyl-2,4(1H, 3H)pyrimidinedionecarbonyl group; an alkylaminocarbonyl group the alkyl group portion of which may be substituted by a halogen atom, hydroxyl group or an alkoxy group; a dialkylaminocarbonyl group the alkyl group portion of which may be substituted by hydroxyl group; an alkoxycarbonyl group optionally substituted by an alkoxy group, hydroxyl group or a halogen atom; an alkylsulfonyl group optionally substituted by hydroxyl group or a halogen atom; an alkenylsulfonyl group; or a dialkylaminosulfonyl group, R¹² is hydrogen atom or an alkyl group, R² is hydrogen atom, Z is oxygen atom or a group represented by —N(R³)—, R³ is an alkyl group optionally substituted by hydroxyl group, and R⁴ is an alkyl group optionally substituted by hydrogen atom or hydroxyl group. Of these, preferred is a compound in which Ring A is a benzene ring represented by the formula:

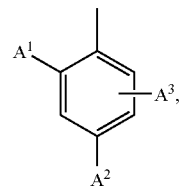

Ring B is a benzene ring represented by the formula:

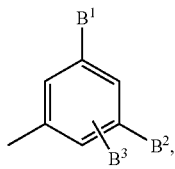

$A^1$ is an alkyl group, $A^2$ is a halogen atom, $A^3$ is hydrogen atom, $B^1$ is a halogen atom or a trihalogenomethyl group, $B^2$ is a halogen atom or a trihalogenomethyl group, $B^3$ is hydrogen atom, $R^1$ is hydroxyl group; an alkylthio group substituted by hydroxyl group; an alkylaminocarbonyloxy group the alkyl group portion of which is substituted by hydroxyl group; an alkylsulfonyl group optionally substituted by hydroxyl group; or a group represented by the formula:

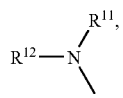

$R^{11}$ is an alkanoyl group substituted by hydroxyl group, and $R^{12}$ is hydrogen atom or an alkyl group.

The compound [I] of the present invention can be used for a pharmaceutical use either in a free form or in a form of a pharmaceutically acceptable salt.

As the pharmaceutically acceptable salt of the compound [I] of the present invention, there may be mentioned, for example, an inorganic acid salt such as hydrochloride, sulfate, phosphate and hydrobromide; and an organic acid salt such as acetate, fumarate, oxalate, citrate, methanesulfonate, benzenesulfonate, tosylate, maleate, succinate and tartarate.

Further, the compound [I] of the present invention or a pharmaceutically acceptable salt thereof includes any of its internal salts, solvates and hydrates, etc.

The compound [I] of the present invention can exist as an optical isomer based on an asymmetric atom, and the present invention includes any of these optical isomers and the mixture thereof. In the present invention, of these optical isomers, a compound in which 2-position (a connection position to the Ring A) of the piperidine ring is an R-configuration is preferred, and a compound in which 2-position (a connection position to the Ring A) of the piperidine ring is an R-configuration and 4-position (a connection position of $R^1$) of the piperidine ring is an S-configuration is particularly preferred.

The compound [I] or a pharmaceutically acceptable salt thereof of the present invention has an excellent tachykinin receptor antagonistic action, particularly an SP receptor antagonistic action, whereby it is useful as a safe medicament for prophylaxis and treatment for inflammation or allergic diseases (for example, atopic dermatitis, dermatitis, herpes, psoriasis, asthma, bronchitis, expectoration, rhinitis, rheumatoid arthritis, osteoarthritis, osteoporosis, multiple sclerosis, conjunctivitis, ophthalmia, cystitis, etc.), pain, migraine, neuralgia, itchiness, cough, and further central nervous system diseases [for example, schizophrenia, Parkinson's disease, depression, anxiety, psychosomatic disorder, morphine dependence, dementia (for example, Alzheimer's disease, etc.), etc.], digestive organs disease [for example, irritable bowel syndrome, ulcerative colitis, Crohn's disease, disorder (for example, gastritis, gastric ulcer, etc.) related to urease-positive *Spirillum* (for example, *helicobacter pylori*, etc.), etc.], nausea, emesis, urinary disorder (for example, pollakiuria, urinary incontinence, etc.), circulatory disease (for example, angina pectoris, hypertension, cardiac failure, thrombosis, etc.) and immune disorder, etc. in mammals (for example, mouse, guinea pig, Mongolian gerbil, ferret, rat, hamster, rabbit, cat, dog, bovine, sheep, monkey, human, etc.). Particularly, since the compound [I] or a pharmaceutically acceptable salt thereof which is an active ingredient of the present invention has a high penetration to the brain and has a low toxicity (high safety), showing almost no side effect, it is useful as a therapeutic or prophylactic agent for central nervous system diseases such as emesis, depression and so forth, or urinary disorder such as pollakiuria, etc.

Measurements on the compound of the present invention or a pharmaceutically acceptable salt thereof can be carried out, according to the method described in European Journal of Pharmacology, vol. 254, pp. 221-227 (1994) with respect to a neurokinin-1 receptor binding action, and according to the method described in European Journal of Pharmacology, vol. 265, pp. 179-183 (1994) with respect to penetration to the brain, and according to the method described in British Journal of Pharmacology, vol. 119, pp. 931-936 (1996) further according to the method described in Journal of Urology, vol. 155, No. 1, pp. 355-360 (1996) with regard to an inhibitory action on pollakiuria.

The compound [I] or a pharmaceutically acceptable salt thereof of the present invention can be administered orally or parenterally, and it can be formulated into a suitable preparation, using a conventionally used pharmaceutical carrier for an oral or parenteral administration. As such a pharmaceutical carrier, there may be mentioned, for example, a binder (syrup, Gum Arabic, gelatin, sorbitol, tragacanth, polyvinylpyrrolidone, etc.), an excipient (lactose, sugar, corn starch, potassium phosphate, sorbitol, glycine, etc.), a lubricant (magnesium stearate, talc, polyethylene glycol, silica, etc.), a disintegrator (potato starch, etc.) and a wetting agent (anhydrous lauryl sodium sulfate, etc.), and the like. Also, when these pharmaceutical preparations are administered orally, they may be a solid preparation such as tablets, granules, capsules and powders, or a liquid preparation such as solution, suspension and emulsion. On the other hand, when they are administered parenterally, for example, they can be administered as an injection solution or an infusion solution, using distilled water for injection, physiological saline, aqueous glucose solution, etc., or they may be administered as a suppository, and the like.

A dose of the compound [I] or a pharmaceutically acceptable salt thereof of the present invention may vary depending on an administration method, an age, a body weight or conditions of a patient, etc., and, for example, in case of oral administration, it is usually administered in a dose of 0.1 to 20 mg/kg per day, and particularly preferably 0.1 to 10 mg/kg per day, and in case of parenteral administration, usually in a dose of 0.01 to 10 mg/kg per day, particularly preferably 0.01 to 1 mg/kg per day.

[Method A]

Among the compounds of the present invention, the compound represented by the formula [I']:

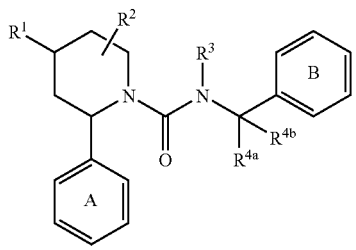

wherein Ring A represents an optionally substituted benzene ring, Ring B represents an optionally substituted benzene ring, $R^1$ represents an optionally substituted alkyl group, an optionally substituted hydroxyl group, a substituted thiol group, a substituted carbonyl group, a substituted sulfinyl group, a substituted sulfonyl group, or a group represented by the formula:

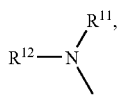

$R^{11}$ represents a substituted carbonyl group or a substituted sulfonyl group, $R^{12}$ represents hydrogen atom or an optionally substituted alkyl group, $R^2$ represents hydrogen atom, an optionally substituted hydroxyl group, an optionally substituted amino group, an optionally substituted alkyl group, a substituted carbonyl group or a halogen atom, $R^3$ represents hydrogen atom or an optionally substituted alkyl group, $R^{4a}$ represents an optionally substituted alkyl group, and $R^{4b}$ represents an optionally substituted alkyl group, can be prepared by, for example, reacting a compound represented by the formula [II]:

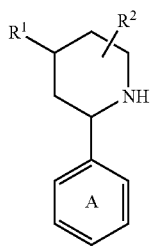

wherein Ring A, $R^1$ and $R^2$ have the same meanings as defined above, and a compound represented by the formula [III]:

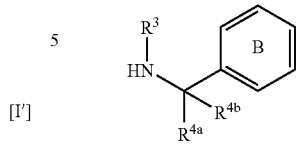

wherein Ring B, $R^3$, $R^{4a}$ and $R^{4b}$ have the same meanings as defined above, in the presence of a urea bond forming agent.

[Method B]

Among the compounds of the present invention, the compound represented by the formula [I-b]:

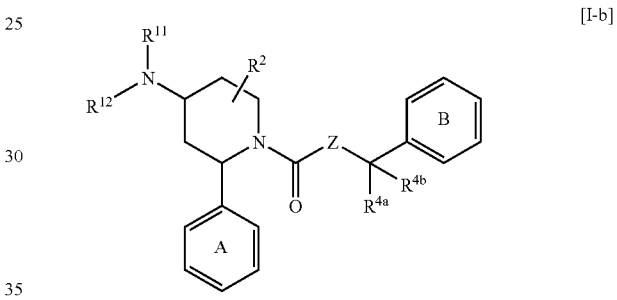

wherein Z represents oxygen atom or a group represented by $—N(R^3)—$, and Ring A, Ring B, $R^{11}$, $R^{12}$, $R^2$, $R^3$, $R^{4a}$ and $R^{4b}$ have the same meanings as defined above, can be prepared by reacting a compound represented by the formula [I-c]:

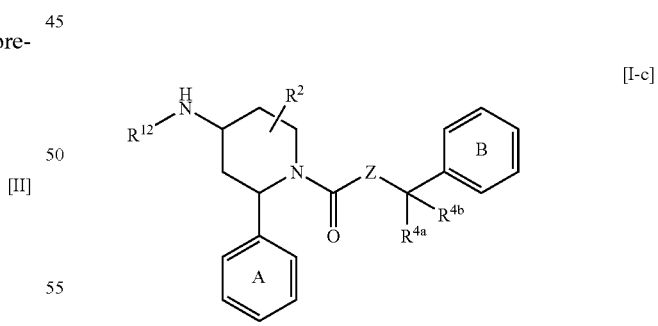

wherein Ring A, Ring B, $R^{12}$, $R^2$, Z, $R^{4a}$ and $R^{4b}$ have the same meanings as defined above, and a compound represented by the formula [VI]:

$$R^{11}—X^2 \quad [VI]$$

wherein $R^{11}$ has the same meaning as defined above, and $X^2$ represents a leaving group.

[Method C]

Among the compounds of the present invention, the compound represented by the formula [I-d]:

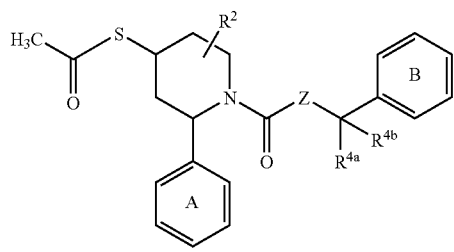

[I-d]

wherein Ring A, Ring B, $R^2$, Z, $R^{4a}$ and $R^{4b}$ have the same meanings as defined above, can be prepared by reacting a compound represented by the formula [VII]:

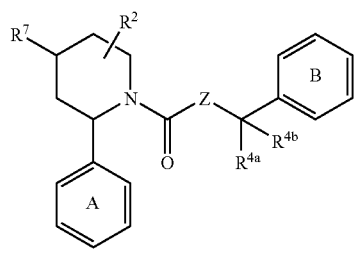

[VII]

wherein Ring A, Ring B, $R^2$, Z, $R^{4a}$ and $R^{4b}$ have the same meanings as defined above, and $R^7$ represents a halogen atom, and a compound represented by the formula [VI-a]:

 [VI-a]

wherein $X^5$ represents hydrogen atom or metal.

[Method D]

Among the objective compounds of the present invention, the compound represented by the formula [I-a]:

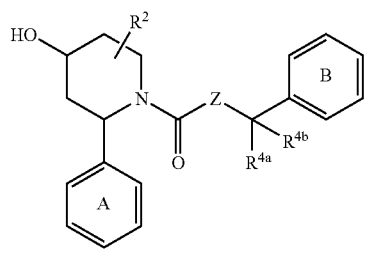

[I-a]

wherein Ring A, Ring B, $R^2$, Z, $R^{4a}$ and $R^{4b}$ have the same meanings as defined above, can be prepared, for example, by reducing a compound represented by the formula [IV]:

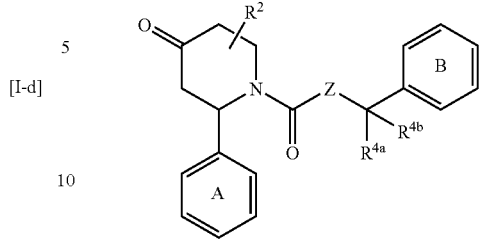

[IV]

wherein Ring A, Ring B, $R^2$, Z, $R^{4a}$ and $R^{4b}$ have the same meanings as defined above.

[Method E]

Among the compounds of the present invention, the compound represented by the formula [I-b]:

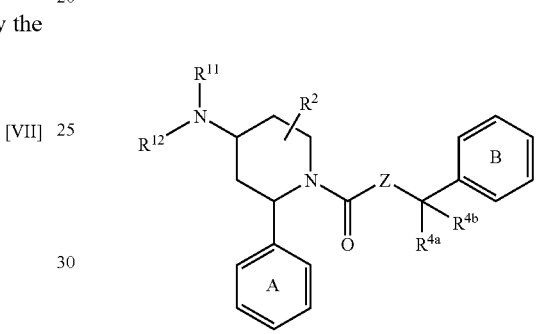

[I-b]

wherein Ring A, Ring B, $R^{11}$, $R^{12}$, $R^2$, Z, $R^{4a}$ and $R^{4b}$ have the same meanings as defined above, can be prepared by reacting a compound represented by the formula [IV]:

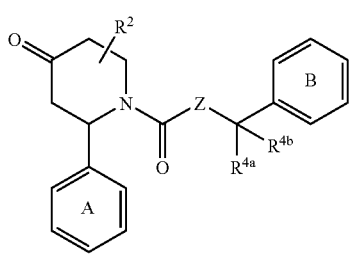

[IV]

wherein Ring A, Ring B, $R^2$, Z, $R^{4a}$ and $R^{4b}$ have the same meanings as defined above, and a compound represented by the formula [V]:

$$\begin{array}{c} R^{11} \\ \diagdown \\ N-X^1 \\ \diagup \\ R^{12} \end{array}$$ [V]

wherein $X^1$ represents hydrogen atom, hydroxyl group, silicon atom, lithium atom or magnesium atom, and $R^{11}$ and $R^{12}$ have the same meanings as defined above.

[Method F]

Among the compounds of the present invention, the compound represented by the formula [I-e]:

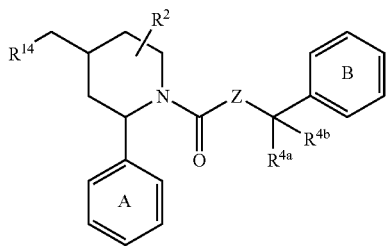

wherein Ring A, Ring B, $R^2$, Z, $R^{4a}$ and $R^{4b}$ have the same meanings as defined above, and $R^{14}$ represents an optionally substituted carboxyl group, can be prepared by reacting a compound represented by the formula [IV]:

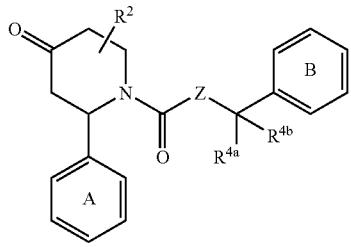

wherein Ring A, Ring B $R^2$, Z, $R^{4a}$ and $R^{4b}$ have the same meanings as defined above, and a compound represented by the formula [VI-b]:

$X^2CH_2R^{14}$ [VI-b]

wherein $X^2$ represents a leaving group, and $R^{14}$ have the same meanings as defined above, and reducing the resulting compound represented by the formula [VIII]:

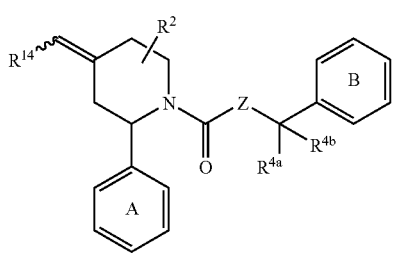

wherein Ring A, Ring B, $R^{14}$, Z, $R^2$, $R^{4a}$ and $R^{4b}$ have the same meanings as defined above.

[Method G]

Among the compounds of the present invention, the compound represented by the formula [I″]:

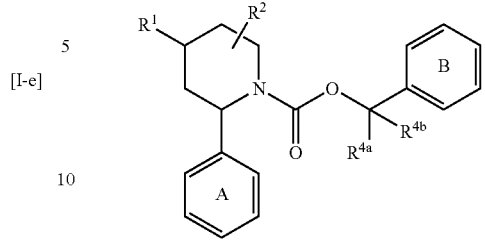

wherein Ring A, Ring B, $R^1$, $R^2$, $R^{4a}$ and $R^{4b}$ have the same meanings as defined above, can be prepared by reacting a compound represented by the formula [II]

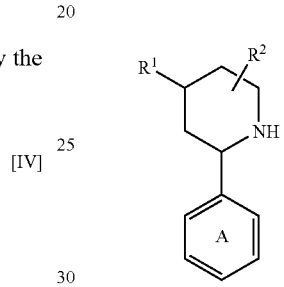

wherein Ring A, $R^1$ and $R^2$ have the same meanings as defined above, and a compound represented by the formula [III′]:

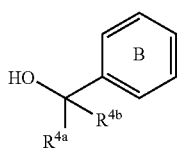

wherein Ring B, $R^{4a}$ and $R^{4b}$ have the same meanings as defined above, in the presence of a urea bond forming agent.

These [Method A] to [Method G] can be carried out as mentioned below.

[Method A]

The reaction between Compound [II] and Compound [III] can be carried out in the presence of a urea bond forming agent in a suitable solvent. As the urea bond forming agent, a compound represented by the formula:

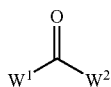

wherein $W^1$ and $W^2$ may be the same or different from each other and each represent a leaving group, may be mentioned. $W^1$ and $W^2$ may be the same or different and each may include imidazolyl group, a halogen atom or phenoxy group. Specifically, 1,1'-carbonyldiimidazole, phosgene, etc. are preferred, and for example, carbonyl dihalide such as 1,1'-carbonyldiimidazole, triphosgene or phosgene, etc. can be used. Also, as the solvent, any solvent may be used so long as it does not exert any bad effect on the reaction, and, for example, acetonitrile, dichloromethane, tetrahydrofuran, etc. may be optionally used. The present reaction can be carried out, for example, at 0° C. to 80° C., preferably at 0° C. to 50° C.

Moreover, the present reaction can be carried out by reacting Compound [II] and an urea bond forming agent represented by the formula:

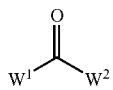

wherein $W^1$ and $W^2$ may be the same or different from each other and each represent a leaving group, to prepare a compound represented by the formula [IX-a]:

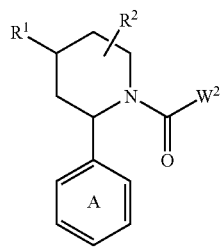

wherein Ring A, $R^1$, $R^2$ and $W^2$ have the same meanings as defined above, then, Compound [IX-a] is led to its reactive derivatives, and reacting it with Compound [III], or reacting Compound [III] with a urea bond forming agent represented by the formula:

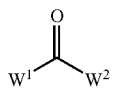

wherein $W^1$ and $W^2$ have the same meanings as defined above, to prepare a compound represented by the formula [IX-b]:

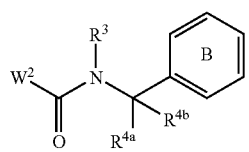

wherein Ring B, $R^3$, $R^{4a}$, $R^{4b}$ and $W^2$ have the same meanings as defined above, then, Compound [IX-b] is led to its reactive derivatives, and reacting it with Compound [II] to prepare Compound [I].

As the reactive derivatives, there may be mentioned, for example, in Compound [IX-a] or Compound [IX-b], a compound in which $W^2$ is led to a group represented by the formula:

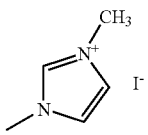

may be mentioned.

The reaction between Compound [II] or Compound [III] and the urea bond forming agent can be carried out, for example, at 0° C. to 80° C., preferably at 0° C. to 50° C. Also, as the solvent, any solvent may be used so long as it does not exert any bad effect on the reaction, and, for example, acetonitrile, dichloromethane, tetrahydrofuran, etc. may be optionally used.

A reaction that lead Compound [IX-a] or Compound [IX-b] to its reactive derivatives can be carried out, for example, by using a reactive derivatizing agent such as methyl iodide at 0° C. to 80° C., preferably at 0° C. to 50° C. Also, as the solvent, any solvent may be used so long as it does not exert any bad effect on the reaction, and, for example, acetonitrile, dichloromethane, tetrahydrofuran, etc. may be optionally used.

The reaction of the respective reactive derivatives and Compound [III] or Compound [II] can be carried out, for example, in the presence of a base at 0° C. to 80° C., preferably at 0° C. to 50° C. Also, as the base, for example, triethylamine, etc. may be used, and as the solvent, any solvent may be used so long as it does not exert any bad effect on the reaction, and, for example, acetonitrile, dichloromethane, tetrahydrofuran, etc. may be optionally used.

[Method B]

The reaction between Compound [I-c] and Compound [VI] can be carried out, for example, when $X^2$ is hydroxyl group, etc., in the presence or absence of a condensing agent and in a suitable solvent. As the condensing agent, 1,1'-carbonylimidazole, 1,3-dicyclohexylcarbodiimide, 1-ethyl-3-(3-dimethylaminopropyl)carbodiimide hydrochloride, isobutyl chloroformate or N-methylmorpholine, etc. may be used, which are used for amide bond forming reaction from a carboxylic acid and an amine. The present reaction can be carried out, for example, at −20° C. to 50° C. Also, for example, when $X^2$ is a halogen atom, etc., it can be carried out, for example, without using a condensing agent, in the presence of a base and in a suitable solvent. As the base, triethylamine, diisopropylethylamine, etc. may be used. Also, as the solvent, any solvent may be used so long as it does not exert any bad effect on the reaction, and, for example, N,N-dimethylformamide, dichloromethane, etc. may be optionally used.

[Method C]

The reaction between Compound [VII] and Compound [VI-a] can be carried out, for example, in a suitable solvent. As the metal of X5, an alkali metal or an alkaline earth metal may be mentioned, and of these, an alkali metal is preferred. As the alkali metal, lithium, potassium and sodium may be mentioned, and as the alkaline earth metal, magnesium, calcium, etc. may be mentioned. The present reaction can be carried out, for example, at −50° C. to 150° C., preferably at 10° C. to 100° C., and as the solvent, any solvent may be used so long as it does not exert any bad effect on the reaction, and, for example, N,N-dimethylformamide, tetrahydrofuran, dichloromethane, acetonitrile, etc. may be optionally used.

[Method D]

Reduction of Compound [IV] can be carried out in the presence of a reducing agent in a suitable solvent. As the reducing agent, sodium borohydride and the like is preferred, and, for example, sodium borohydride, aluminum hydride such as diisobutylaluminum hydride, sodium bis(2-methoxyethoxy)aluminum hydride, etc. ma be used. Also, as the solvent, any solvent may be used so long as it does not exert any bad effect on the reaction, and, for example, ethanol, tetrahydrofuran, dichloromethane, etc. may be optionally used. The present reaction can be carried out, for example, at −70° C. to under reflux, preferably at −70° C. to 20° C.

[Method E]

The reaction of Compound [IV] and Compound [V] can be carried out by applying them to reductive amination in a suitable solvent. This reductive amination can be carried out under acidic conditions by effecting hydrogenation with a reducing agent such as sodium borohydride, triacetoxy sodium borohydride, sodium cyanoborohydride, etc. or a reducing catalyst such as palladium, etc. As the group [$X^1$] of Compound [V], hydrogen atom or hydroxyl group is preferred, and, for example, hydrogen atom, hydroxyl group, silicon atom, lithium atom or magnesium atom may be mentioned. As the solvent, any solvent may be used so long as it does not exert any bad effect on the reaction, and, for example, dichloromethane, acetic acid, ethanol, methanol, etc. may be optionally used. As a salt of Compound [V], hydrochloride, acetate, etc. may be optionally used. The present reaction can be carried out, for example, at −10° C. to 80° C., preferably at 0° C. to 30° C.

[Method F]

The reaction between Compound [IV] and Compound [VI-b] can be carried out, for example, in the presence of a base and in a suitable solvent. As the leaving group [$X^2$] of Compound [VI-b], diethylphosphono group, triphenyl-phosphinyl group, etc. may be mentioned. As the base, for example, potassium-tert-butoxide, triethylamine, sodium hydroxide, etc. may be mentioned, and as the solvent, any solvent may be used so long as it does not exert any bad effect on the reaction, for example, tetrahydrofuran, dichloromethane, etc. may be optionally used. The present reaction can be carried out, for example, at −30° C. to 80° C., preferably at −20° C. to 30° C.

Also, reduction of Compound [VIII] can be carried out according to the conventional manner to effect hydrogenation with a reducing catalyst such as palladium, etc. As the solvent, methanol, ethanol, etc. may be optionally used. The present reaction can be carried out, for example, at 0° C. to 50° C.

[Method G]

The reaction between Compound [II] and Compound [III'] can be carried out in the presence of a urea bond forming agent and in a suitable solvent. As the urea bond forming agent, a compound represented by the formula:

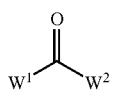

wherein $W^1$ and $W^2$ have the same meanings as defined above, may be mentioned. As $W^1$ and $W^2$, they may be the same or different from each other, and each may include imidazolyl group, a halogen atom or phenoxy group. Specifically, 1,1'-carbonyldiimidazole, phosgene, etc. are preferred, and, for example, carbonyl dihalide such as 1,1'-carbonyldiimidazole, triphosgene or phosgene, etc. may be used. Also, as the solvent, any solvent may be used so long as it does not exert any bad effect on the reaction, and, for example, acetonitrile, dichloromethane, tetrahydrofuran, etc. may be optionally used. The present reaction can be carried out, for example, at 0° C. to 80° C., preferably at 0° C. to 50° C.

Moreover, the present reaction can be carried out by reacting Compound [II] and a urea bond forming agent represented by the formula:

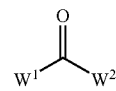

wherein $W^1$ and $W^2$ have the same meanings as defined above, to prepare a compound of the formula [IX-a]:

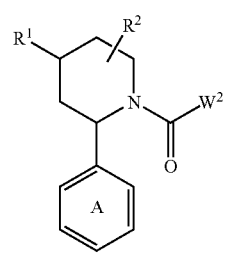

[IX-a]

wherein Ring A, $R^1$, $R^2$ and $W^2$ have the same meanings as defined above, then, Compound [IX-a] is led to its reactive derivatives, and reacting it with Compound [III'], or reacting Compound [III'] with a urea bond forming agent represented by the formula:

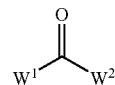

wherein $W^1$ and $W^2$ have the same meanings as defined above, to prepare a compound represented by the formula [IX']:

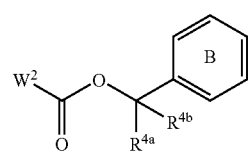

[IX']

wherein Ring B, $R^{4a}$, $R^{4b}$ and $W^2$ have the same meanings as defined above, then, Compound [IX'] is led to its reactive derivatives, and reacting it with Compound [II] to prepare Compound [I″]

As the reactive derivatives, there may be mentioned, for example, in Compound [IX-a] or Compound [IX'], a compound in which $W^2$ is led to a group represented by the formula:

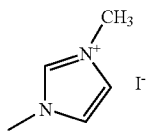

may be mentioned.

The reaction between Compound [II] or Compound [III'] and the urea bond forming agent can be carried out, for example, at 0° C. to 80° C., preferably at 0° C. to 50° C. Also, as the solvent, any solvent may be used so long as it does not exert any bad effect on the reaction, and, for example, acetonitrile, dichloromethane, tetrahydrofuran, etc. may be optionally used.

A reaction that lead Compound [IX-a] or Compound [IX'] to its reactive derivatives can be carried out, for example, by using a reactive derivatizing agent such as methyl iodide at 0° C. to 80° C., preferably at 0° C. to 50° C. Also, as the solvent, any solvent may be used so long as it does not exert any bad effect on the reaction, and, for example, acetonitrile, dichloromethane, tetrahydrofuran, etc. may be optionally used.

The reaction of the respective reactive derivatives and Compound [III'] or Compound [II] can be carried out, for example, in the presence of a base at 0° C. to 80° C., preferably at 0° C. to 50° C. Also, as the base, for example, triethylamine, etc. may be used, and as the solvent, any solvent may be used so long as it does not exert any bad effect on the reaction, and, for example, acetonitrile, dichloromethane, tetrahydrofuran, etc. may be optionally used.

The objective Compound [I] of the present invention can be also prepared by converting the group $R^1$ and the group $R^3$ of the compound obtained as mentioned above into the other substituent(s) Such a converting method of the substituent(s) can be suitably selected depending on the kinds of the substituents to be converted, for example, it can be carried out by the following (Method a) to (Method q).

(Method a): In the formula [I], the objective Compound [I] in which the group $R^1$ is a substituent (for example, an optionally substituted alkoxy group, an optionally substituted carbonyloxy group or alkylsulfonyloxy group, etc.) containing a substituted hydroxyl group can be prepared by subjecting a corresponding compound containing hydroxyl group in the group $R^1$ to alkylation, acylation or sulfonylation according to the conventional manner. For example, the alkylation can be carried out at –10° C. to 80° C., the acylation can be carried out at 5° C. to 80° C., and the sulfonylation can be carried out at 5° C. to 80° C.

(Method b): In the formula [I], the objective Compound [I] in which the group $R^1$ is a substituent containing an optionally substituted amino group can be prepared by substituting a corresponding compound having amino group at the group $R^1$ with a substituent for the amino group (for example, an alkoxycarbonyl group such as tert-butoxycarbonyl group, etc., an arylalkoxycarbonyl group such as benzyloxycarbonyl group, etc., an alkanoyl group such as formyl group, acetyl group, propionyl group, etc., an alkyl group such as methyl group, ethyl group, propyl group, etc., an alkylsulfonyl group such as methanesulfonyl group, ethanesulfonyl group, etc., an alkenylsulfonyl group such as vinylsulfonyl group, etc., a heterocyclic group such as pyridyl group, etc.) according to the conventional manner, or by using a carbamate synthesizing reagent such as N,N'-succinimidylcarbonate, etc., and reacting with, for example, alkoxyalkyl alcohol, etc. The substitution can be optionally carried out depending on the kind of the substituent(s), according to the conventional manner such as alkylation, acylation, sulfonylation, allylation, etc. Moreover, the hydrogen atom of the amino group is substituted by a substituent to prepare a di-substituted compound. The present reaction can be carried out at –20° C. to 50° C.

Also, in case where the objective Compound [I] in which the group $R^1$ is a substituent containing an optionally substituted amino group is a compound having a urea bond, such a compound can be prepared by using a corresponding amine compound and a urea bond forming agent, and the reaction is carried out in the same manner as in [Method A] or according to the method as described in Japanese Unexamined Patent Publication No. Hei. 10-195037.

Moreover, in the formula [I], the objective Compound [I] in which the group $R^1$ is a substituent containing an optionally substituted amino group can be prepared by adding a compound containing amino group to a corresponding compound containing a carbon-carbon double bond at the group $R^1$ according to the conventional manner. The present reaction can be carried out, for example, under reflux of a solvent or in the absence of a solvent.

(Method c): In the formula [I], the objective Compound [I] in which the group $R^1$ contains amino group can be prepared from a corresponding Compound [I] in which the group $R^1$ is a protected amino group by removing (deprotecting) the protective group. Removal of the protective group can be carried out according to the conventional manner (for example, acid treatment, base treatment, catalytic reduction, etc.). Among the present reactions, the reaction using an acid treatment can be carried out, for example, at 5° C. to 120° C., the reaction by a base treatment can be carried out at 50° C. to 40° C., and the reaction by a catalytic reduction can be carried out at 10° C. to 40° C.

Also, in the formula [I], the objective Compound [I] in which the group $R^1$ contains amino group can be prepared by reducing a corresponding Compound [I] in which the group $R^1$ contains nitro group. The reduction can be carried out by reacting tin dichloride, zinc, etc., in the presence of an acid. The present reaction can be carried out, for example, by refluxing a solvent.

Moreover, in the formula [I], the objective Compound [I] in which the group $R^1$ contains amino group can be prepared by applying a corresponding Compound [I] in which the group $R^1$ contains carboxyl group to Curtius rearrangement, etc. Curtius rearrangement can be carried out, for example, by the method described in Advanced Organic Chemistry, $4^{th}$ Edition, p. 1054. That is, the carboxyl group is converted into an acid chloride by using thionyl chloride, etc., then, making it an azide by sodium azide, etc., and subjecting to hydrolysis.

(Method d): In the formula [I], the objective Compound [I] in which the group $R^1$ contains hydroxyl group can be prepared by removing a protective group from a corresponding Compound [I] in which the group $R^1$ contains a protected hydroxyl group according to the conventional manner. Removal of the protective group can be carried out according to an acid treatment, a base treatment, a catalytic reduction, etc. depending on the kind of the protective group. The present reaction proceeds suitably, for example, at 0° C. to 80° C., particularly at 5° C. to 50° C.

Also, in the formula [I], the objective Compound [I] in which the group $R^1$ contains hydroxyl group can be prepared by reducing a corresponding Compound [I] in which the group $R^1$ contains formyl group. The reduction can be carried out by reacting the compounds in the presence of a reducing agent such as sodium borohydride, etc. The present reaction proceeds suitably, for example, at −80° C. to 80° C., particularly at −70° C. to 20° C.

Moreover, in the formula [I], the objective Compound [I] in which the group $R^1$ contains hydroxyl group can be prepared by reducing a corresponding Compound [I] in which the group $R^1$ contains an ester or carboxyl group. The reduction can be carried out by reacting the compounds in the presence of a reducing agent such as lithium aluminum hydride. The present reaction proceeds suitably, for example, at −50° C. to 200° C., particularly at −20° C. to 60° C.

(Method e): In the formula [I], when the group $R^1$ is hydroxyl group, and the compound has an asymmetric center at the binding portion of the $R^1$, the steric configuration can be converted into the reverse configuration according to, for example, the method of Mitsunobu et al. (Synthesis, pp. 1 to 28, 1981). Specifically, the conversion is carried out in the presence of triphenylphosphine, benzoic acid and diethylazodicarboxylate in a suitable solvent. The present reaction proceeds suitably, for example, at 0° C. to 60° C., particularly at SOC to 40° C.

(Method f): In the formula [I], the objective Compound [I] in which the group $R^1$ contains an optionally substituted thiol group can be prepared by reacting a corresponding Compound [I] in which the group $R^1$ has hydroxyl group and a corresponding compound containing thiol group, for example, according to the method of Mitsunobu et al. (Synthesis, pp. 1 to 28, 1981). Specifically, the reaction can be carried out in the presence of triphenylphosphine and diethylazodicarboxylate in a suitable solvent. The present reaction can be carried out, for example, under reflux of a solvent.

In the formula [I], the objective Compound [I] in which the group $R^1$ contains optionally substituted thiol group can be prepared by reacting a corresponding Compound [I] in which the group $R^1$ contains a halogen atom and a corresponding compound containing thiol group. The present reaction proceeds suitably, for example, at −50° C. to 150° C., particularly at 10° C. to 100° C.

In addition, the objective compound in which the group $R^1$ contains an alkylthio group can be also prepared by subjecting a corresponding Compound [I] in which the group $R^1$ contains thiol group or a corresponding compound in which the thiol group is protected (for example, an acetylated thiol group) to alkylation in the presence of a base. The present reaction proceeds suitably, for example, at −10° C. to 80° C., particularly at 5° C. to 50° C.

(Method g): In the formula [I], the objective Compound [I] in which the group $R^1$ contains an optionally substituted amino group can be prepared by subjecting a corresponding Compound [I] in which the group $R^1$ contains hydroxyl group to amination according to, for example, the method of Mitsunobu et al. (Synthesis, pp. 1 to 28, 1981).

(Method h): In the formula [I], the objective Compound [I] in which the group $R^1$ contains free carboxyl group can be prepared by subjecting a corresponding Compound [I] in which the group $R^1$ contains an esterified carboxyl group to deesterification (for example, depending on the kind of the ester residue, hydrolysis by a base such as sodium hydroxide, etc., acid treatment using trifluoroacetic acid, hydrogen chloride, hydrogen bromide, etc., reduction under hydrogen atmosphere, using palladium (black), palladium carbon, etc., and the like) according to the conventional manner. Among the present deesterification reactions, for example, hydrolysis using a base can be carried out at 5° C. to 70° C., acid treatment can be carried out at 5° C. to 80° C., and reduction can be carried out at 10° C. to 40° C.

(Method i): In the formula [I], the objective Compound [I] in which the group $R^1$ contains an amide bond can be prepared by reacting a corresponding Compound [I] in which the group $R^1$ contains free carboxyl group and a corresponding amine compound, or a corresponding Compound [I] in which the group $R^1$ contains free amino group and a corresponding carboxylic acid compound, in the presence or absence of a condensing agent. The condensing agent may include 1,1'-carbonyldiimidazole, 1,3-dicyclohexylcarbodiimide, 1-ethyl-3-(3-dimethylaminopropyl)carbodiimide hydrochloride, isobutyl chloroformate or N-methylmorpholine, etc., which can be usually used in the amide-bond forming reaction from a carboxylic acid and an amine. The present reaction can be carried out, for example, at −20° C. to 50° C.

(Method j): In the formula [I], the objective Compound [I] in which the group $R^1$ is a group containing a heterocyclic group in which the nitrogen atom of the substituent is substituted by oxo group (nitrogen atom is oxidized) (for example, N-oxomorpholino group, etc.) can be prepared by treating a corresponding Compound [I] in which the group $R^1$ is a group containing a heterocyclic group with an oxidizing agent (for example, 3-chloroperbenzoic acid, hydrogen peroxide, peracetic acid, OXONE, etc.). The present reaction proceeds suitably, for example, at 5° C. to 50° C.

(Method k): In the formula [I], the objective Compound [I] in which the group $R^1$ is a group containing a heterocyclic group where the nitrogen atom is oxidized (for example, N-alkyl-4-morpholinio group, etc.) other than the above-mentioned (Method j) can be prepared by reacting a corresponding Compound [I] in which the group $R^1$ is a group containing a heterocyclic group and an alkyl halide. The present reaction proceeds suitably, for example, at 20° C. to 80° C.

(Method l): In the formula [I], the objective Compound [I] in which the group $R^3$ is an alkyl group can be prepared by subjecting a corresponding Compound [I] in which the group $R^3$ is hydrogen atom to alkylation according to the conventional manner. The alkyl group may be optionally substituted. The present reaction proceeds suitably, for example, at 20° C. to 80° C.

(Method m): In the formula [I], the objective Compound [I] in which the group $R^1$ is a group containing a group in which the sulfur atom in the substituent is substituted by an oxo group (for example, sulfinyl group, etc.) can be prepared by treating a corresponding Compound [I] in which the group $R^1$ is a group containing thio group with an oxidizing agent (for example, 3-chloroperbenzoic acid, peracetic acid, sodium periodate, OXONE, etc.). The present reaction proceeds suitably, for example, at −80° C. to 150° C., particularly at 0° C. to 40° C.

(Method n): In the formula [I], the objective Compound [I] in which the group $R^1$ is a group containing a group in which the sulfur atom in the substituent is substituted by two oxo groups (for example, sulfonyl group, etc.) can be prepared by treating a corresponding Compound [I] in which the group $R^1$ is a group containing thio group with an oxidizing agent (for example, 3-chloroperbenzoic acid, peracetic acid, sodium periodate, OXONE, etc.). The present reaction proceeds suitably, for example, at −80° C. to 150° C., particularly at 0° C. to 40° C.

(Method o): In the formula [I], the objective Compound [I] in which the group $R^1$ is a group containing amino group can be prepared by applying a corresponding Compound [I] in which the group $R^1$ is a group containing carbonyl group to reductive amination. The present reaction can be carried out in the same manner as in the above-mentioned [Method E]

(Method p): In the formula [I], the objective Compound [I] in which the group $R^1$ contains sulfinic acid can be prepared by treating a corresponding Compound [I] in which the group $R^1$ contains an alkylsulfinyl group, for example, according to a literature (Synlett, No. 4, pp. 375-377, 1997).

(Method q): In the formula [I], the objective Compound [I] in which the group $R^1$ contains imidazolidinyl group or hexahydropyrimidinyl group can be prepared by subjecting a corresponding compound in which the group $R^1$ contains an aminoalkylamino group to cyclization. The present reaction can be carried out, for example, in the presence of a condensing agent such as 1,1'-carbonyldiimidazole, etc. The present reaction can be carried out, for example, at −20° C. to 50° C.

The solvent to be used in the above-mentioned (Method a) to (Method q) is not specifically limited so long as it does not inhibit the reaction, and, for example, there may be optionally used by selecting from dioxane, ethylene glycol dimethyl ether, dimethylacetamide, dimethylformamide, hexamethyl phosphoramide, benzene, tetrahydrofuran, toluene, ethyl acetate, alcohol, dichloromethane, carbon tetrachloride, 1,3-dimethyl-2-imidazolidine, acetic acid, diethyl ether, methoxyethane, dimethylsulfoxide, acetonitrile, water or a mixed solvent of the above solvents.

Incidentally, the starting Compound [IV] of the present invention is a novel compound, and can be prepared, for example, by the following chemical reaction formula.

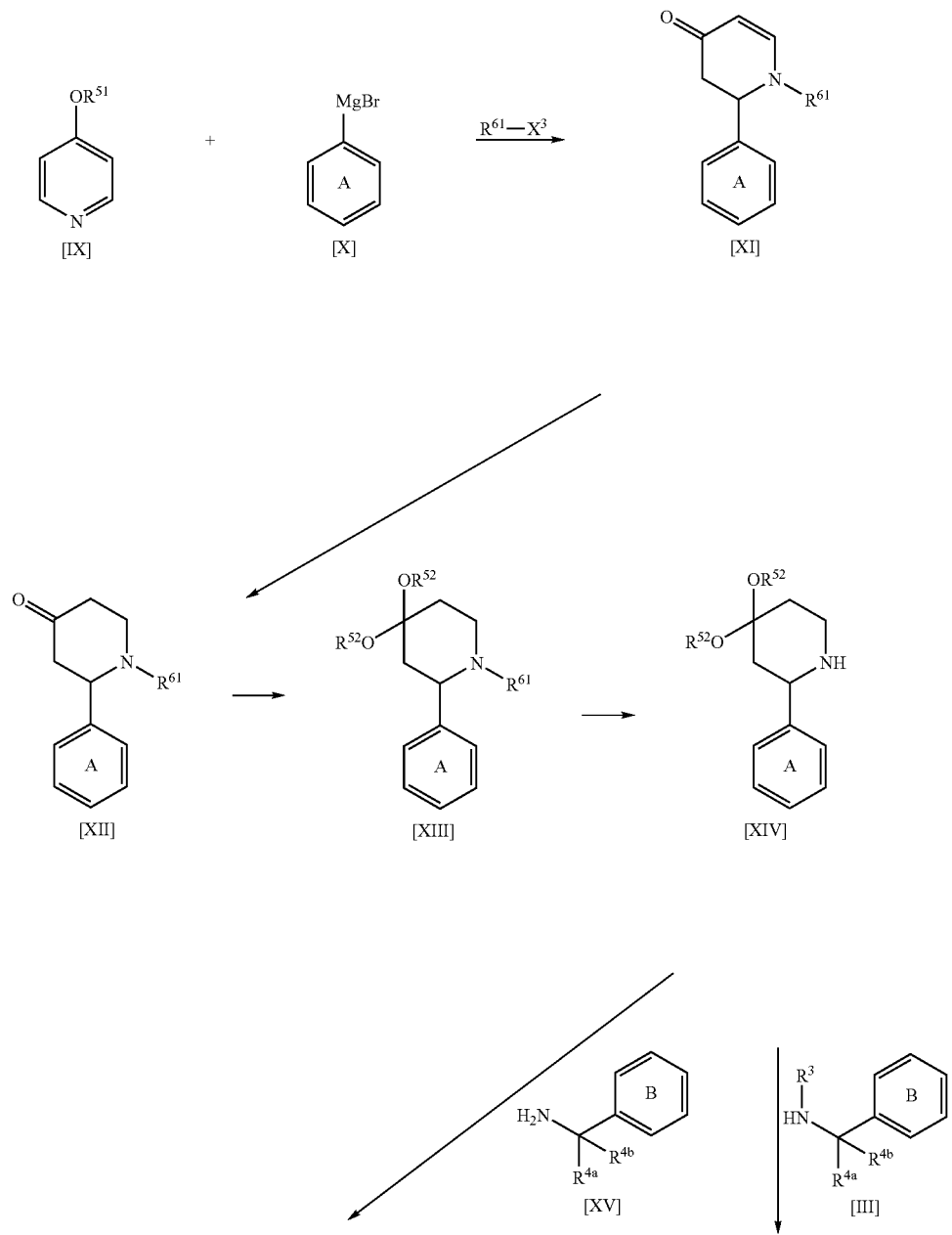

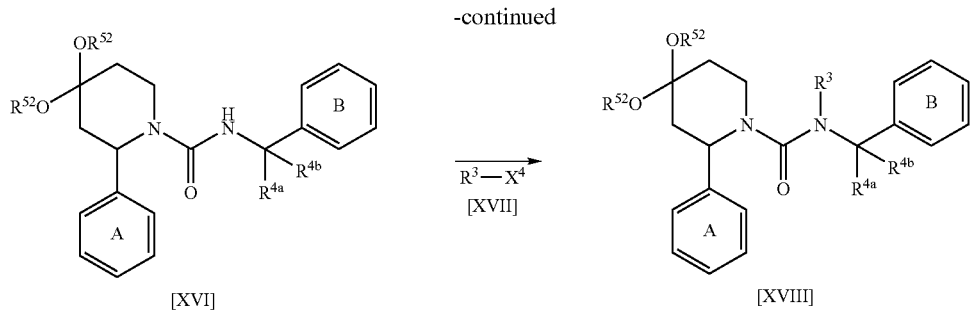

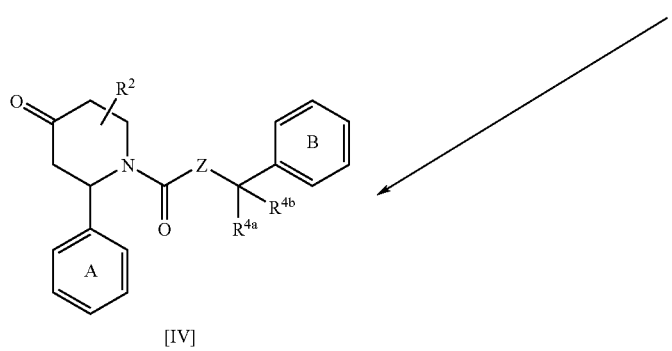

wherein $R^{51}$ represents an alkyl group, $R^{61}$ represents a protective group for amino group, $R^{52}$ represents an alkyl group which may be bonded at the terminal, $X^3$ represents a leaving group, $X^4$ represents a leaving group, and Ring A, Ring B, $R^3$, $R^{4a}$ and $R^{4b}$ have the same meanings as defined above.

That is, the pyridine compound [IX] and the Grignard Compound [X] are condensed, and the amino group is protected to obtain Compound [XI], then, applying the compound to reduction to obtain Compound [XII]. Moreover, the carbonyl group of Compound [XII] is protected by ketal to prepare Compound [XIII], and the protective group of the amino group is removed to obtain Compound [XIV]. Then, Compound [XIV] and Compound [XV] are applied to condensation to obtain Compound [XVI], and the compound is reacted with Compound [XVII], or Compound [XIV] and Compound [III] are applied to condensation and the protective group of the obtained Compound [XVIII] is removed to obtain Compound [IV].

The starting Compound [III] of the present invention can be prepared, for example, by the following chemical reaction formula.

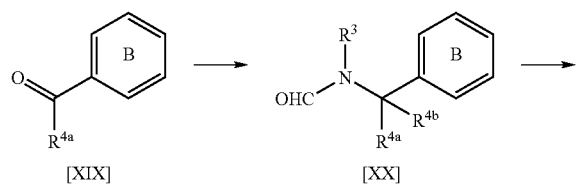

wherein Ring B, $R^3$, $R^{4a}$ and $R^{4b}$ have the same meanings as defined above.

That is, Compound [XIX] is applied to Grignard reaction, and then, applied to isonitrilation reaction. The obtained compound is hydrolyzed to obtain Compound [XX], and then, Compound [XX] is subjected to deformylation reaction to obtain Compound [III].

Compound [IV] has an asymmetric carbon, and an optical isomer exists based on the asymmetric carbon, and by using an optical isomer of the above-mentioned Compound [XIV], a desired optical isomer Compound [IV] can be obtained.

An optical isomer of Compound [XIV] can be obtained by optically resolving a racemic mixture of Compound [XIV] according to the conventional manner. Optical resolution can be carried out, for example, by acting Compound [XIV] and N-acyl-optically active amino acid or N-sulfonyl-optically active amino acid, and one of the diastereomer salt is separated and collected by utilizing solubility difference between the formed two kinds of diastereomer salts.

Acyl group of the N-acyl-optically active amino acid may be mentioned, for example, acetyl group, propionyl group, tosyl group or benzyloxycarbonyl group, and the optically active amino acid may be mentioned, for example, L-phenylalanine, L-leucine, L-glutamine, L-methionine, L-valine, L-threonine, D-phenylalanine or D-phenylglycine.

Also, among the starting Compound [II] of the present invention, Compound [II-a] can be prepared, for example, by the following chemical reaction formula.

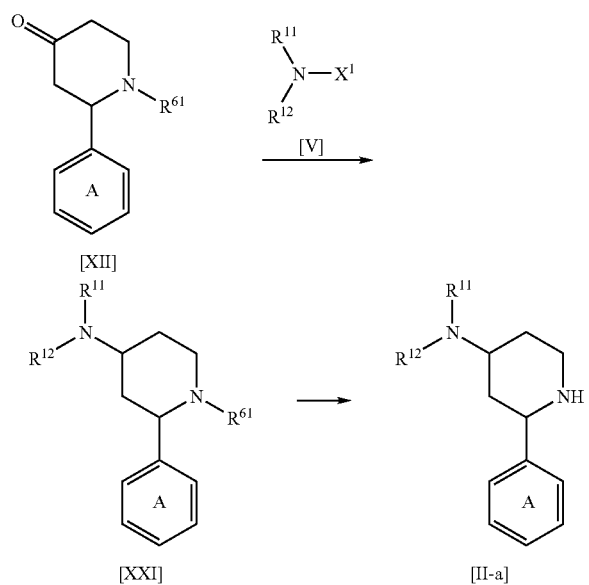

wherein Ring A, $R^{11}$, $R^{12}$, $R^{61}$ and $X^1$ have the same meanings as defined above.

That is, Compound [XII] and Compound [V] are applied to reductive amination, and the protective group of the amino group of the obtained Compound [XXI] is removed to give Compound [II-a]. Reductive amination can be carried out in the same manner as in [Method E].

For preparing the above-mentioned Compound [IV], the respective intermediate compounds may be optionally used not only those shown in the chemical reaction formula but also its salt or reactive derivatives thereof as long as it does not participate in the reaction.

Also, among the starting compounds of the present invention, the compound represented by the formula [XXII]:

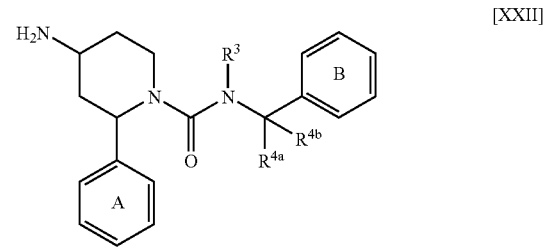

wherein Ring A, Ring B, $R^3$, $R^{4a}$ and $R^{4b}$ have the same meanings as defined above, can be prepared as mentioned below.

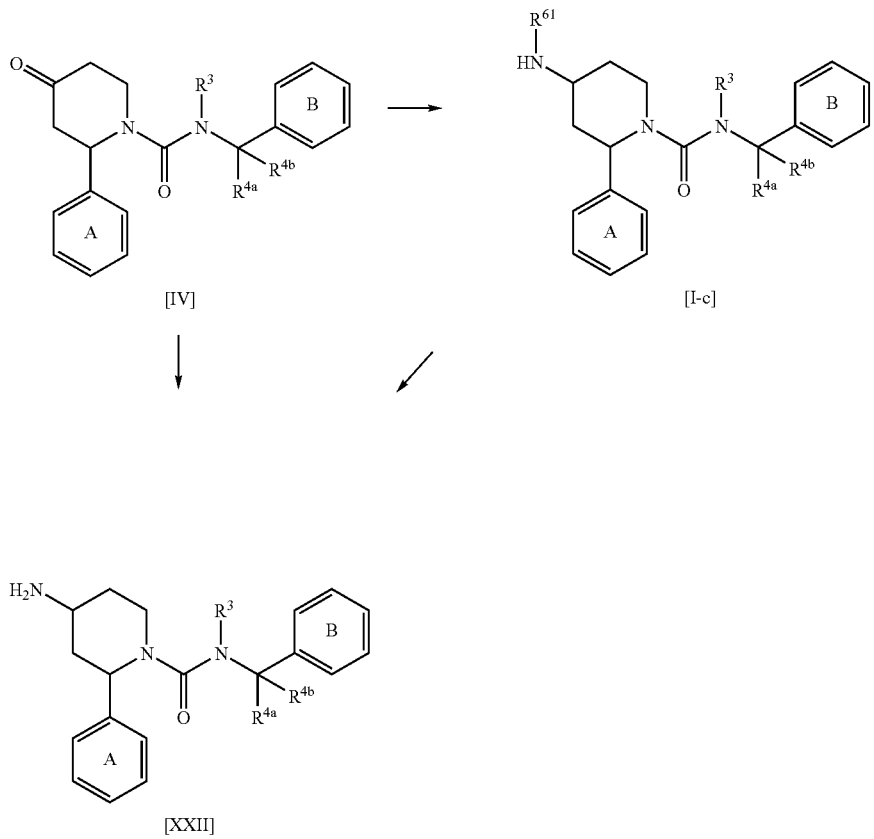

wherein Ring A, Ring B, $R^3$, $R^{4a}$, $R^{4b}$ and $R^{61}$ have the same meanings as defined above.

That is, Compound [IV] is applied to reductive amination, and the protective group of the amino group is removed from the obtained Compound [I-c] to obtain Compound [XXII], or Compound [IV] and ammonia are used to apply them to reductive amination, Compound [XXII] can be obtained.

Also, among the starting compounds of the present invention, the compound represented by the formula [II-b]:

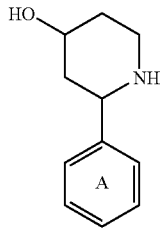

[II-b]

wherein Ring A has the same meaning as defined above, and the compound represented by the formula [II-c]:

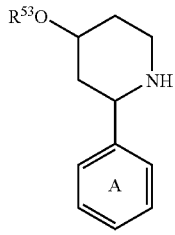

[II-c]

wherein $R^{53}$ represents a substituent, and Ring A has the same meaning as defined above, can be prepared as mentioned below.

As the substituent of $R^{53}$, a substituent in which $R^1$ is an optionally substituted hydroxyl group may be mentioned.

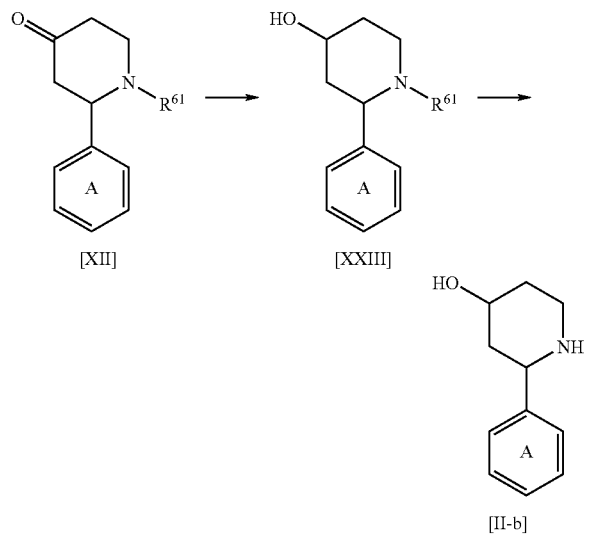

wherein Ring A and $R^{61}$ have the same meanings as defined above.

That is, Compound [XII] is reduced to obtain Compound [XXIII], and removal of the protective group of the amino group of the obtained Compound [XXIII] is carried out to prepare Compound [II-b].

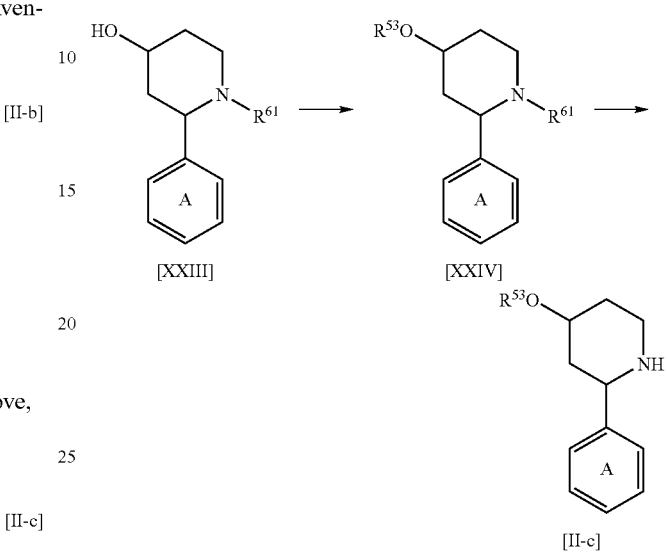

wherein Ring A, $R^{53}$ and $R^{61}$ have the same meanings as defined above.

Also, Compound [II-c] can be prepared by introducing a substituent into the hydroxyl group of Compound [XXIII] obtained as mentioned above to obtain Compound [XXIV], and removing the protective group of the amino group of the obtained Compound [XXIV].

In Compounds [II-b] and [II-c], optical isomers exist, and according to the same method of the optical resolution of the above-mentioned Compound [XIV], they can be prepared by subjecting to optical resolution from racemic mixtures.

Moreover, for preparing the objective compounds and starting compounds of the present invention, when the starting compounds or the respective intermediate compounds have a functional group(s), a suitable protective group is introduced into the respective functional group(s) according to the conventional manner of synthetic chemistry other than those as mentioned above, and, if they are not necessary, these protective groups may be optionally removed.

In the present specification, the alkyl group means a straight or branched alkyl group having 1 to 6 carbon atoms such as methyl group, ethyl group, propyl group, isopropyl group, butyl group, isobutyl group, tert-butyl group, isopentyl group, etc., preferably that having 1 to 4 carbon atoms. The alkenyl group means a straight or branched alkenyl group having 2 to 7 carbon atoms such as vinyl group, allyl group, propenyl group, isopropenyl group, etc., preferably that having 2 to 4 carbon atoms. The alkoxy group means a straight or branched an alkoxy group having 1 to 6 carbon atoms such as methoxy group, ethoxy group, propoxy group, isopropoxy group, butoxy group, etc., preferably that having 1 to 4 carbon atoms, and the alkanoyl group means a straight or branched alkanoyl group having 1 to 6 carbon atoms such as formyl group, acetyl group, propionyl group, butyryl group, valeryl group, tertbutylcarbonyl group, etc., preferably that having 1 to 4 carbon atoms. The cycloalkyl group means a cycloalkyl group having 3 to 8 carbon atoms such as cyclopropyl group, cyclobutyl group, cyclopentyl group, cyclohexyl group, cycloheptyl group, cyclooctyl group, etc., preferably that having 3 to 6 carbon atoms. Moreover, the halogen atom may be mentioned chlorine, bromine, iodine or fluorine.

EXAMPLE

Example 1

To 50 ml of a tetrahydrofuran solution containing 2.8 g of N-{1-(3,5-bistrifluoromethyl)phenyl-1-methyl}ethyl-N-methylamine was added 3.2 g of 1,1'-carbonyldiimidazole, and the mixture was stirred under reflux for 16 hours. After completion of the reaction, the solvent was removed by distillation, chloroform and water were added to the residue and the mixture was separated. The organic layer was further washed twice with water, dried and concentrated. To 50 ml of an acetonitrile solution of the residue was added 3 ml of methyl iodide, and the mixture was stirred at 70° C. for 2 hours. The reaction solution was concentrated, 50 ml of tetrahydrofuran was added to the residue, to the solution were successively added 2.1 g of (2R,4S)-4-hydroxy-2-(4-fluoro-2-methylphenyl)piperidine and 1.5 ml of triethylamine, and the mixture was stirred at 70° C. for 16 hours. The reaction solution was concentrated, chloroform and water were added to the residue and the mixture was separated. The organic layer was washed again, dried and concentrated. The residue was purified by silica gel column chromatography (n-hexane:ethyl acetate=3:2) to give 2.2 g of (2R,4S)-1-[N-{1-(3,5-bistrifluoromethylphenyl-1-methyl)ethyl}-N-methyl]aminocarbonyl-2-(4-fluoro-2-methyl-phenyl)-4-hydroxypiperidine shown in the following Table 1.

Example 2

To 5 ml of a tetrahydrofuran solution containing 132 mg of (2R,4S)-1-[N-{1-(3,5-bistrifluoromethylphenyl-1-methyl)ethyl}-N-methyl]aminocarbonyl-2-(4-fluoro-2-methyl-phenyl)-4-hydroxypiperidine was added 42 mg of 1,1'-carbonyldiimidazole, and the mixture was stirred under reflux for 2 hours. Further, 0.3 ml of ethanolamine was added to the mixture, the mixture was stirred at the same temperature for 1 hour, and the reaction solution was concentrated. The residue was purified by silica gel column chromatography (n-hexane:ethyl acetate=1:1) to give 123 mg of (2R,4S)-1-[N-{1-(3,5-bistrifluoromethylphenyl-1-methyl)ethyl}-N-methyl]aminocarbonyl-2-(4-fluoro-2-methyl-phenyl)-4-(2-hydroxyethylaminocarbonyloxy)piperidine shown in the following Table 1.

Examples 3-4

By using corresponding starting compounds, the same treatments as in Example 2 were carried out to give the compounds shown in the following Table 1.

Example 5

(1) To 20 ml of a tetrahydrofuran solution containing 2.0 g of (2R,4S)-1-[N-{1-(3,5-bistrifluoromethylphenyl-1-methyl)-ethyl}-N-methyl]aminocarbonyl-2-(4-fluoro-2-methylphenyl)-4-hydroxypiperidine were added 1.66 g of carbon tetrabromide and 1.31 g of triphenylphosphine, and the mixture was stirred at room temperature for 2 hours. To the solution was added 80 ml of diethyl ether, the mixture was stirred and precipitated insoluble materials were removed by filtration. The filtrate was concentrated, and the residue was purified by silica gel chromatography (n-hexane:ethyl acetate=20:1→10:1) to give 2 g of (2R,4R)-4-bromo-1-[N-{1-(3,5-difluorophenyl-1-methyl)ethyl}-N-methyl]aminocarbonyl-2-(4-fluoro-2-methylphenyl)piperidine shown in the following Table 1.

(2) To 20 ml of an N,N-dimethylformamide solution containing 2 g of the compound obtained in the above-mentioned (1) was added 1.14 g of potassium thioacetate, and the mixture was stirred at 80° C. overnight. The reaction solution was concentrated, ethyl acetate was added thereto, and the organic layer was washed with water and saturated brine, dried and concentrated. The residue was purified by silica gel chromatography (n-hexane:ethyl acetate=19:1→3:1) to give 1.5 g of (2R,4S)-4-acetylthio-1-[N-{1-(3,5-difluorophenyl-1-methyl)ethyl}-N-methyl]aminocarbonyl-2-(4-fluoro-2-methylphenyl)piperidine shown in the following Table 1.

(3) To 2 ml of a methanol solution containing 290 mg of the compound obtained in the above-mentioned (2) were added 0.2 ml of methyl iodide and 2 ml of an aqueous 2M sodium hydroxide solution, and the mixture was stirred at room temperature overnight. To the reaction solution was added an aqueous citric acid solution to neutralize the solution, and methanol was removed by distillation. To the residue was added chloroform, and the mixture was washed, dried and concentrated. The residue was purified by silica gel chromatography (n-hexane:ethyl acetate=6:1) to give 230 mg of (2R,4S)-1-[N-{1-(3,5-difluorophenyl-1-methyl)ethyl}-N-methyl]aminocarbonyl-2-(4-fluoro-2-methylphenyl)-4-methylthiopiperidine shown in the following Table 1.

(4) To 5 ml of a chloroform solution containing 125 mg of the compound obtained in the above-mentioned (3) was added 200 mg of 3-chloroperbenzoic acid, and the mixture was stirred at room temperature overnight. To the solution was added sodium thiosulfate pentahydrate, the mixture was extracted with chloroform, and the extract was dried and concentrated. The residue was purified by silica gel chromatography (chloroform:methanol=19:1) to give 120 mg of (2R,4S)-1-[N-{1-(3,5-difluorophenyl-1-methyl)ethyl}-N-methyl]aminocarbonyl-2-(4-fluoro-2-methylphenyl)-4-methanesulfonylpiperidine shown in the following Table 1.

Example 6

By using corresponding starting compounds, the same treatments as in Example 5(1)-(3) were carried out to give (2R,4S)-1-[N-{1-(3,5-difluorophenyl-1-methyl)ethyl}-N-methyl]aminocarbonyl-2-(4-fluoro-2-methylphenyl)-4-(2-hydroxyethylthio)piperidine shown in the following Table 1.

Examples 7-10

By using corresponding starting compounds, the same treatments as in Example 5(1)-(4) were carried out to give compounds shown in the following Table 1 and Table 2.

Example 11

To 5 ml of an N,N-dimethylformamide solution containing 104 mg of (2R,4S)-4-amino-1-[N-{1-(3,5-bistrifluoromethylphenyl-1-methyl)ethyl}-N-methyl]aminocarbonyl-2-(4-fluoro-2-methylphenyl)piperidine were added 25 mg of 3-hydroxy-3-methylbutanoic acid, 31 mg of 1-ethyl-3-(3-dimethylaminopropyl)carbodiimide hydrochloride and 38 mg of 1-hydroxy-1H-benzotriazole, and the reaction solution was stirred at room temperature overnight. The reaction solution was extracted with ethyl acetate, the organic layer was washed twice with saturated brine, dried and concentrated.

The residue was purified by silica gel column chromatography (n-hexane:ethyl acetate=4:1→2:3) to give 103 mg of (2R,4S)-1-[N-{1-(3,5-bistrifluoromethylphenyl-1-methyl)-ethyl}-N-methyl]aminocarbonyl-2-(4-fluoro-2-methylphenyl)-4-(3-hydroxy-3-methylbutyroylamino)piperidine shown in the following Table 2.

Example 12

By using corresponding starting compounds, the same treatments as in Example 11 were carried out to give (2R,4S)-1-[N-{1-(3,5-bistrifluoromethylphenyl-1-methyl)-ethyl}-N-methyl]aminocarbonyl-2-(4-fluoro-2-methylphenyl)-4-{N-(3-hydroxy-3-methylbutyroyl)-N-methylamino}piperidine shown in the following Table 2.

Example 13

By using corresponding starting compounds, the same treatments as in Example 1 were carried out to give (2R,4S)-1-[N-{1-(3,5-difluorophenyl-1-methyl)ethyl}-N-methyl]aminocarbonyl-2-(4-fluoro-2-methylphenyl)-4-hydroxypiperidine shown in the following Table 3.

Example 14

By using corresponding starting compounds, the same treatments as in Example 2 were carried out to give (2R,4S)-1-[N-{1-(3,5-difluorophenyl-1-methyl)ethyl}-N-methyl]aminocarbonyl-2-(4-fluoro-2-methylphenyl)-4-(2-hydroxyethylaminocarbonyloxy)piperidine shown in the following Table 3.

Examples 15-17

By using corresponding starting compounds, the same treatments as in Example 5(1)-(4) were carried out to give compounds shown in the following Table 3.

Reference Example 1

(1) In 200 ml of diethyl ether was dissolved 12.8 g of 3,5-bistrifluoromethylacetophenone, the solution was cooled to −20° C., and 20 ml of 3M methyl Grignard-diethyl ether solution was added dropwise thereto. The reaction solution was stirred for 1 hour, an aqueous ammonium chloride solution, water and ethyl acetate were added to the solution and the resulting mixture was further stirred for 10 minutes. By separating the liquids, the organic layer was recovered, washed with saturated brine, dried and concentrated to give oily product. The obtained oily product was dissolved in 25 ml of trimethylsilyl cyanide, the solution was cooled to −20° C., 16 ml of conc. sulfuric acid was added dropwise to the solution and the resulting mixture was stirred for 1 hour. The reaction solution was added dropwise into ice, 80 ml of 1 M aqueous sodium hydroxide solution was added thereto and the mixture was stirred. This solution was extracted with chloroform, the organic layer was dried over magnesium sulfate and concentrated. The residue was dissolved in 100 ml of N,N-dimethylformamide, and the solution was cooled to 0-5° C. To the solution was added 4 g of sodium hydride (60% oily), then, 10 ml of methyl iodide was added thereto, and the resulting mixture was stirred at 0-5° C. for 2 hours. To the reaction solution were successively added water and ethyl acetate, and the mixture was stirred and then the liquids were separated. The organic layer was washed with water, dried over magnesium sulfate and concentrated. The residue was purified by silica gel column chromatography (n-hexane:ethyl acetate=2:1) to give 13.5 g of {N-{1-(3,5-bistrifluoromethylethyl)phenyl-1-methyl}ethyl}-N-methyl}formamide.

(2) To 100 ml of an ethanol solution containing 13.5 g of the compound obtained in the above-mentioned (1) was added 100 ml of conc. aqueous hydrogen bromide solution (49%), and the mixture was stirred at 60° C. for 2 hours. The reaction solution was gradually added dropwise to a sufficiently cooled aqueous sodium carbonate solution. This mixed solution was extracted twice with chloroform, sodium chloride was added to the aqueous layer and the mixture was extracted again with chloroform. The whole organic layer was dried over sodium sulfate, and concentrated to give 11.2 g of N-{1-(3,5-bistrifluoromethyl)phenyl-1-methyl}-ethyl}-N-methylamine shown in the following Table 4.

Reference Example 2

(1) To Grignard solution prepared from 14.2 g of magnesium, 93.1 g of 2-bromo-5-fluorotoluene and 500 ml of tetrahydrofuran was added dropwise 50 ml of 4-methoxypyridine at −20° C. under nitrogen stream. After dropwise addition, the mixture was stirred at the same temperature for 20 minutes. Moreover, the reaction solution was cooled to −50° C., and 85 ml of benzyldichlorocarbonate was added dropwise to the solution while maintaining the temperature to −40° C. or lower. After dropwise addition, the temperature of the reaction solution was gradually raised, 200 g of ice was added thereto at −15° C. and the mixture was stirred for 30 minutes. Moreover, 200 ml of 5M aqueous citric acid solution was added thereto, and the mixture was stirred at room temperature for 1 hour. Tetrahydrofuran was removed from the reaction solution under reduced pressure, 200 ml of ethyl acetate was added to the residue and the mixture was extracted twice. The whole organic layer was washed with an aqueous sodium hydrogen carbonate solution, and with saturated brine, dried and concentrated. The residue was collected by filtration with isopropyl ether, and washed to give 146.5 g of 1-benzyloxycarbonyl-2-(4-fluoro-2-methylphenyl)-4-oxo-2,3-dihydro-1H-pyridine.

(2) To 4600 ml of an acetic acid solution containing 190 g of 1-benzyloxycarbonyl-2-(4-fluoro-2-methylphenyl)-4-oxo-2,3-dihydro-1H-pyridine was added 91 g of zinc powder, and the mixture was stirred at room temperature for 24 hours. Insoluble materials were filtered off from the reaction solution, and the filtrate was concentrated. To the residue was added 400 ml of ethyl acetate, and the mixture was washed with an aqueous sodium hydrogen carbonate solution and saturated brine, dried and concentrated. The residue was purified by silica gel column chromatography (ethyl acetate:hexane=2:1) to give 166 g of 1-benzyloxycarbonyl-2-(4-fluoro-2-methylphenyl)-4-oxopiperidine.

(3) To 132 g of the compound obtained in the above-mentioned (2) were added 650 ml of methanol, 84 ml of trimethoxymethane and 2 g of strongly acidic resin, IR-120 (available from ORGANO Corporation), and the mixture was stirred at room temperature for 3 days. Insoluble materials were filtered off from the reaction solution, and the filtrate was concentrated to give 146 g of 1-benzyloxycarbonyl-2-(4-fluoro-2-methylphenyl)-4,4-dimethoxypiperidine.

(4) To 300 ml of ethanol were added 30 g of the compound obtained in the above-mentioned (3) and 3 g of 10% palladium-carbon, and the mixture was stirred at room temperature under hydrogen atmosphere for 3 hours. Insoluble materials were filtered off from the reaction solution, the filtrate was concentrated, and 300 ml of ethyl acetate was added to the residue. Under ice-cooling, 20 ml of 4M hydrochloric acid-ethyl acetate solution was gradually added dropwise thereto. Crystals were collected by filtration, and washed with ethyl acetate. After drying, the crystals were added to dichloromethane-aqueous sodium carbonate, and the mixture was stirred. The organic layer was separated, and the aqueous layer was extracted again with dichloromethane. The whole organic layer was dried and concentrated to give 16.7 g of 2-(4-fluoro-2-methylphenyl)-4,4-dimethoxypiperidine.

(5) 35 ml of methanol was added to 130 ml of an ethyl acetate suspension containing 10.1 g of the compound obtained in the above-mentioned (4) and 3.18 g of L-N-acetylvaline, and after dissolving the mixture under heating, the mixture was allowed to cool at room temperature. After 3.5 hours, precipitated crystals were collected by filtration, washed with 20 ml of ethyl acetate, and the obtained crystals were dried under reduced pressure. Next, 50 ml of chloroform was added thereto, the organic layer was washed with 30 ml of 2M aqueous sodium hydroxide solution, and 30 ml of saturated brine, dried and concentrated. Ether was added to the residue, precipitated crystals were further dried under reduced pressure to give 2.94 g of (2R)-(4-fluoro-2-methylphenyl)-4,4-dimethoxypiperidine (Optical purity: 97.0% ee).

(6) In 300 ml of tetrahydrofuran and 180 ml of water was dissolved 30 g of (2R)-(4-fluoro-2-methylphenyl)-4,4-dimethoxypiperidine, 20.3 ml of benzyloxycarbonyl chloride and 15.06 g of sodium carbonate were added to the solution under ice-cooling, and the mixture was stirred for 2 hours. To the reaction solution were added ethyl acetate and water, the liquids were separated, the organic layer was washed with saturated brine, dried and concentrated to give 50.9 g of (2R)-1-benzyloxycarbonyl-4,4-dimethoxy-2-(4-fluoro-2-methylphenyl)-piperidine.

(7) In 570 ml of tetrahydrofuran was dissolved 50.9 g of the compound obtained in the above-mentioned (6), 230 ml of 1 M aqueous sulfuric acid solution was added to the solution under ice-cooling, and the mixture was stirred at 0-5° C. for 4 hours. A pH of the mixture was adjusted to 8 to 9 with 1 M aqueous sodium hydroxide solution, tetrahydrofuran was removed by distillation, water and ethyl acetate were added to the residue and the liquids were separated. The aqueous layer was extracted with ethyl acetate, and the whole organic layer was washed with saturated brine, dried and concentrated. The residue was purified by silica gel chromatography (hexane:chloroform:ethyl acetate=10:10:1→5:5:1) to give 39.8 g of (2R)-1-benzyloxycarbonyl-2-(4-fluoro-2-methylphenyl)-4-oxopiperidine.

(8) To 300 ml of a methanol solution containing 34.2 g of the compound obtained in the above-mentioned (7) was blown ammonia gas at −78° C. for 30 minutes, and the mixture was stirred at room temperature for 18 hours. The mixture was again cooled to −60° C., ammonia gas was blown therein for 30 minutes, 1.9 g of sodium borohydride was added to the mixture, and the temperature of the mixture was raised to room temperature. Distilled water was added to the reaction solution, the mixture was concentrated under reduced pressure, and the residue was extracted with ethyl acetate, dried and concentrated. The residue was dissolved in 200 ml of diethyl ether, to the solution was added 22 g of ditert-butyldicarbonate, and the mixture was stirred at room temperature for 18 hours. Distilled water was added to the reaction solution, the mixture was extracted with ethyl acetate, and the organic layer was washed with saturated brine, dried and concentrated. The residue was purified by silica gel chromatography (hexane:ethyl acetate=3:1→2:1) to give 23.6 g of (2R)-1-benzyloxycarbonyl-4-tertbutoxycarbonylamino-2-(4-fluoro-2-methylphenyl)piperidine.

(9) In 25 ml of methanol was dissolved 23.6 g of the compound obtained in the above-mentioned (8), 5 g of palladium-carbon was added to the solution, and the mixture was stirred under hydrogen atmosphere at 101 kPa for 2 hours. After completion of the reaction, the mixture was filtered, and the filtrate was concentrated. The residue was purified by NH-silica gel column chromatography (n-hexane:ethyl acetate=1:1) to give 15.7 g of (2R,4S)-4-butoxycarbonylamino-2-(4-fluoro-2-methylphenyl)piperidine shown in the following Table 4.

Reference Example 3

(1) To 100 ml of tetrahydrofuran solution containing 2.85 g of N-{1-(3,5-bistrifluoromethylphenyl)-1-methylethyl}-N-methylamine was added 3.2 g of 1,1'-carbonyldiimidazole, and the mixture was stirred under reflux for 20 minutes. The reaction solution was concentrated, and extracted with chloroform. The organic layer was dried and concentrated. The residue was dissolved in 50 ml of acetonitrile, 3 ml of methyl iodide was added to the solution and the mixture was stirred at 70° C. for 2 hours, and the reaction solution was concentrated. To 50 ml of a dichloromethane solution containing the residue were added 3.1 g of (2R,4S)-4-butoxycarbonylamino-2-(4-fluoro-2-methylphenyl)piperidine and 1.4 ml of triethylamine, and the mixture was stirred at 70° C. overnight. The reaction solution was poured into water, and the liquids were separated. The aqueous layer was extracted with ethyl acetate, and the whole organic layer was washed with saturated brine, dried and concentrated. The residue was purified by silica gel chromatography (hexane:ethyl acetate=9:1→1:1) to give 2.4 g of (2R,4S)-1-[N-{1-(3,5-bistrifluoromethylphenyl-1-methyl)ethyl}-N-methyl]aminocarbonyl-4-butoxycarbonylamino-2-(4-fluoro-2-methylphenyl)piperidine.

(2) To 310 mg of the compound obtained in the above-mentioned (1) was added 2 ml of 4M hydrochloric acid-ethyl acetate solution, the solution was concentrated under reduced pressure, sodium hydroxide and dichloromethane were added to the residue and the liquids were separated. The organic layer was concentrated to give 200 mg of (2R,4S)-4-amino-1-[N-{1-(3,5-bistrifluoromethylphenyl-1-methyl)ethyl}-N-methyl]aminocarbonyl-2-(4-fluoro-2-methylphenyl)piperidine shown in the following Table 4.

Reference Example 4

To 5 ml of an N,N-dimethylformamide solution containing 620 mg of (2R,4S)-1-[N-{1-(3,5-bistrifluoromethylphenyl-1-methyl)ethyl}-N-methyl]aminocarbonyl-4-butoxycarbonylamino-2-(4-fluoro-2-methylphenyl)piperidine were successively added 40 mg of sodium hydride and 0.5 ml of methyl iodide under ice-cooling, and the mixture was stirred for 1 hour. After completion of the reaction, an aqueous citric acid solution, brine and ethyl acetate were added to the mixture and the liquids were separated. The organic layer was further washed with brine, dried and concentrated. The residue was treated in the same manner as in Reference example 3(2), and the residue was purified by NH-silica gel column chromatography (hexane:ethyl acetate=1:1) to give 400 mg of (2R,4S)-1-[N-{1-(3,5-bistrifluoromethylphenyl-1-methyl)ethyl}-N-methyl]aminocarbonyl-4-methylamino-2-(4-fluoro-2-methylphenyl)piperidine shown in the following Table 4.

Reference Example 5

(1) Corresponding starting compounds were treated in the same manner as in Reference example 1(1) to give N-{1-(3,5-difluorophenyl-1-methyl)ethyl}-N-methylformamide.

(2) To 8.5 g of the compound obtained in the above-mentioned (1) was added 100 ml of 6M aqueous hydrochloric acid solution, and the mixture was stirred at 110° C. for 1 hour. To the reaction solution was added 500 ml of 2M aqueous sodium hydroxide solution, the mixture was stirred, and extracted twice with diethyl ether. The whole organic layer was dried over sodium sulfate and concentrated. The residue was purified by NH-silica gel column chromatography (n-hexane:ethyl acetate=10:1) to give 5 g of N-{1-(3,5-difluorophenyl-1-methyl)ethyl}-N-methylamine shown in the following Table 4.

Reference Example 6

In 5 ml of methanol was dissolved 0.639 g of N-tosyl-D-phenylalanine, the solution was heated to 59° C., and 0.418 g of 2-(4-fluoro-2-methyl)phenyl-4-hydroxypiperidine dissolved in 1.3 ml of methanol was added dropwise to the solution. At the time at which crystals were started to precipitate, crystals were grown for 20 minutes, and the remaining methanol solution of 2-(4-fluoro-2-methyl)phenyl-4-hydroxypiperidine was added dropwise thereto over 5 minutes. Thereafter, the temperature thereof was cooled from 59° C. to 30° C. over 1 hour, and crystals were further grown over 1 hour under stirring conditions. The obtained crystals were collected by filtration, washed with ice-cold methanol, and dried at 60° C. overnight under ventilation to give 0.325 g of a diastereomer salt of (2R,4S)-2-(4-fluoro-2-methyl)phenyl-4-hydroxypiperidine. To the obtained crystals was added 0.62 ml of 2M hydrochloric acid, ethyl acetate was added thereto and the liquids were separated. To the aqueous layer was added 0.3 ml of 5M aqueous sodium hydroxide solution, and the mixture was extracted four times with ethyl acetate (1 ml). The organic layer was dried and concentrated to give 0.129 g of (2R,4S)-2-(4-fluoro-2-methyl)phenyl-4-hydroxypiperidine shown in the following Table 4.

TABLE 1

[Structure: piperidine core with R¹ at 4-position, 2-(4-fluoro-2-methylphenyl) substituent, N-carbonyl-N(CH₃)-C(CH₃)₂-(3,5-bis(trifluoromethyl)phenyl) group]

| Example No. | R¹ | MS |
|---|---|---|
| 1 | HO—CH₂— | 521 (M⁺ + 1) |
| 2 | HO-CH₂CH₂-NH-C(O)-O-CH₃ | 608 (M⁺ + 1) |
| 3 | (S)-HO-CH(CH₃)-CH₂-NH-C(O)-O-CH₃ | 622 (M⁺ + 1) |
| 4 | (R)-HO-CH(CH₃)-CH₂-NH-C(O)-O-CH₃ | 622 (M⁺ + 1) |
| 5(1) | Br— (with stereochemistry) | 585 (M⁺ + 1) |
| 5(2) | H₃C-C(O)-S-CH₂— | 589 (M⁺ + 1) |
| 5(3) | H₃CS-CH₂— | 551 (M⁺ + 1) |
| 5(4) | H₃C-S(O)₂-CH₂— | 583 (M⁺ + 1) |
| 6 | HO-CH₂CH₂-S-CH₂— | 581 (M⁺ + 1) |
| 7 | (H₃C)₂CH-S(O)₂-CH₂— | 611 (M⁺ + 1) |

TABLE 2

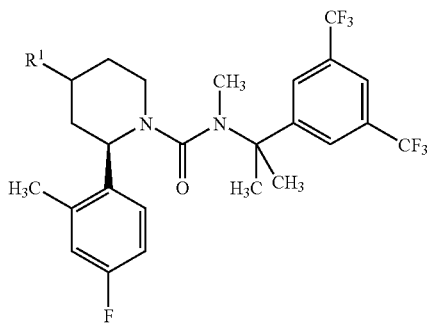

| Example No. | R¹ | MS |
|---|---|---|
| 8 | HO−CH₂CH₂−S(O)₂−CH₃ | 613 (M⁺ + 1) |
| 9 | (CH₃)₂C(OH)−CH₂−S(O)₂−CH₃ | 641 (M⁺ + 1) |
| 10 | (R)-CH₃CH(OH)−CH₂−S(O)₂−CH₃ | 627 (M⁺ + 1) |
| 11 | (CH₃)₂C(OH)−CH₂−C(O)−NH−CH₃ | 620 (M⁺ + 1) |
| 12 | (CH₃)₂C(OH)−CH₂−C(O)−N(CH₃)₂ | 634 (M⁺ + 1) |

TABLE 3

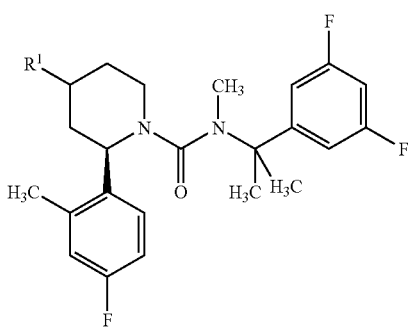

| Example No. | R¹ | MS |
|---|---|---|
| 13 | HO−CH₂− | 421 (M⁺ + 1) |
| 14 | HO−CH₂CH₂−NH−C(O)−O−CH₃ | 508 (M⁺ + 1) |
| 15 | H₃C−S(O)₂− | 483 (M⁺ + 1) |
| 16 | HO−CH₂CH₂−S(O)₂−CH₃ | 513 (M⁺ + 1) |
| 17 | (CH₃)₂C(OH)−CH₂−S(O)₂−CH₃ | 541 (M⁺ + 1) |

TABLE 4

| Reference example No. | Structural formula | MS |
|---|---|---|
| 1(2) | 3,5-bis(CF₃)-C₆H₃-C(CH₃)₂-NH-CH₃ | 286 (M⁺ + 1) |

TABLE 4-continued

| Reference example No. | Structural formula | MS |
|---|---|---|
| 2(9) | | 309 (M⁺ + 1) |
| 3(2) | | 520 (M⁺ + 1) |
| 4 | | 534 (M⁺ + 1) |
| 5(2) | | 186 (M⁺ + 1) |
| 6 | | 210 (M⁺ + 1) |

UTILIZABILITY IN INDUSTRY

The compounds of the present invention have an excellent tachykinin receptor antagonistic action. Also, the compounds of the present invention have high safety, and excellent in the points of absorption, penetration to the brain, stability in metabolism, concentration in blood, sustainability, etc., and thus, have excellent medical effects.

What is claimed is:

1. Piperidine compound represented by the formula [I]:

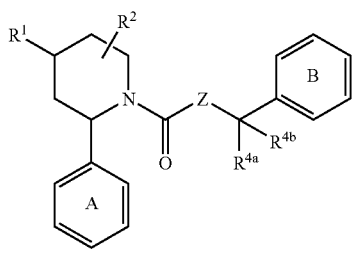

wherein Ring A and Ring B each represents a benzene ring optionally substituted by halogen or $C_1$-$C_4$ alkyl optionally substituted with fluoro groups, $R^1$ represents an optionally substituted alkyl group, an optionally substituted hydroxyl group, a substituted thiol group, a substituted carbonyl group, a substituted sulfinyl group, a substituted sulfonyl group, or a group represented by the formula:

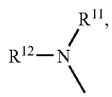

$R^{11}$ represents a substituted carbonyl group or a substituted sulfonyl group, $R^{12}$ represents hydrogen atom or an optionally substituted alkyl group, $R^2$ represents hydrogen atom, Z represents a group represented by —N($R^3$)—, $R^3$ represents a methyl group, $R^{4a}$ represents a methyl group, $R^{4b}$ represents a methyl group, or a pharmaceutically acceptable salt thereof.

2. The compound according to claim 1, wherein $R^1$ is an optionally substituted alkyl group.

3. The compound according to claim 1, wherein $R^1$ is an optionally substituted hydroxyl group.

4. The compound according to claim 1, wherein $R^1$ is thiol group substituted by a substituent(s).

5. The compound according to claim 1, wherein $R^1$ is a substituted carbonyl group.

6. The compound according to claim 1, wherein $R^1$ is a substituted sulfinyl group.

7. The compound according to claim 1, wherein $R^1$ is a substituted sulfonyl group.

8. The compound according to claim 1, wherein $R^1$ is a group represented by the formula:

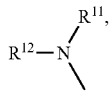

$R^{11}$ represents a substituted carbonyl group or a substituted sulfonyl group, and $R^{12}$ represents hydrogen atom or an optionally substituted alkyl group.

9. A process for preparing a piperidine compound represented by the formula [I']:

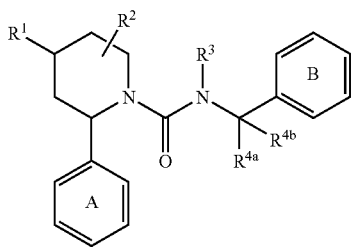

wherein each of Ring A and Ring B represents a benzene ring optionally substituted with halogen or $C_1$-$C_4$ alkyl optionally substituted with fluoro groups, $R^1$ represents an optionally substituted alkyl group, an optionally substituted hydroxyl group, a substituted thiol group, a substituted carbonyl group, a substituted sulfinyl group, a substituted sulfonyl group, or a group represented by the formula:

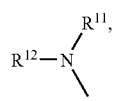

$R^{11}$ represents a substituted carbonyl group or a substituted sulfonyl group, $R^{12}$ represents hydrogen atom or an optionally substituted alkyl group, $R^2$ represents hydrogen atom, an optionally substituted hydroxyl group, an optionally substituted amino group, an optionally substituted alkyl group, a substituted carbonyl group or a halogen atom, $R^3$ represents hydrogen atom or an optionally substituted alkyl group, $R^{4a}$ represents an optionally substituted alkyl group, $R^{4b}$ represents an optionally substituted alkyl group, or a pharmaceutically acceptable salt thereof, which comprises reacting a compound represented by the formula [II]:

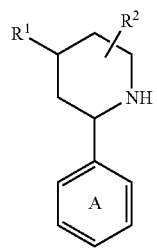

wherein Ring A, $R^1$ and $R^2$ have the same meanings as defined above, and a compound represented by the formula [III]:

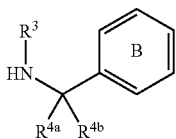

[III]

wherein Ring B, $R^3$, $R^{4a}$ and $R^{4b}$ have the same meanings as defined above, in the presence of a urea bond forming agent, and then, optionally, converting it into a pharmaceutically acceptable salt thereof.

10. A process for preparing a piperidine compound represented by the formula [I-b]:

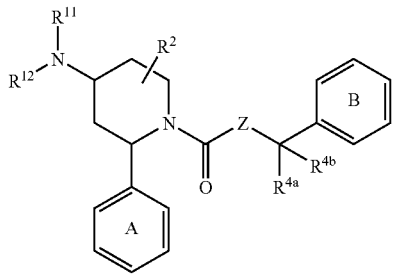

[I-b]

wherein Ring A and Ring B each represents benzene ring optionally substituted with halogen or $C_1$-$C_4$ alkyl optionally substituted with fluoro groups, $R^{11}$ represents a substituted carbonyl group or a substituted sulfonyl group, $R^{12}$ represents hydrogen atom or an optionally substituted alkyl group, $R^2$ represents hydrogen atom, an optionally substituted hydroxyl group, an optionally substituted amino group, an optionally substituted alkyl group, a substituted carbonyl group or a halogen atom, Z represents a group represented by —N($R^3$)—, $R^3$ represents hydrogen atom or an optionally substituted alkyl group, $R^{4a}$ represents an optionally substituted alkyl group, $R^{4b}$ represents an optionally substituted alkyl group, or a pharmaceutically acceptable salt thereof, which comprises reacting a compound represented by the formula [I-c]:

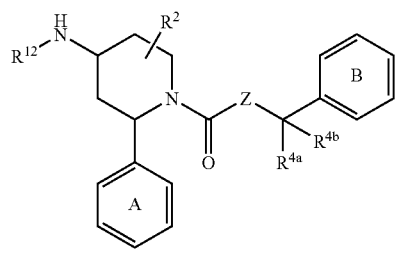

[I-c]

wherein Ring A, Ring B, $R^{12}$, $R^2$, Z, $R^{4a}$ and $R^{4b}$ have the same meanings as defined above, and a compound represented by the formula [VI]:

$R^{11}$—$X^2$ [VI]

wherein $R^{11}$ has the same meaning as defined above, and $X^2$ represents an eliminating group, and then optionally, converting it into a pharmaceutically acceptable salt thereof.

* * * * *